US012064455B2

(12) United States Patent
Stefansson et al.

(10) Patent No.: US 12,064,455 B2
(45) Date of Patent: Aug. 20, 2024

(54) FREE FATTY ACIDS AND METHODS OF MANUFACTURE AND USE FOR TREATING CORONAVIRUS AND OTHER VIRAL RESPIRATORY INFECTIONS

(71) Applicant: LIPID PHARMACEUTICALS EHF, Reykjavik (IS)

(72) Inventors: Einar Stefansson, Reykjavik (IS); Thorsteinn Loftsson, Reykjavik (IS)

(73) Assignee: LIPID PHARMACEUTICALS EHF, Reykjavik (IS)

( * ) Notice: Subject to any disclaimer, the term of this patent is extended or adjusted under 35 U.S.C. 154(b) by 57 days.

(21) Appl. No.: 17/206,041

(22) Filed: Mar. 18, 2021

(65) Prior Publication Data

US 2021/0290692 A1 Sep. 23, 2021

Related U.S. Application Data

(60) Provisional application No. 63/073,757, filed on Sep. 2, 2020, provisional application No. 62/991,368, filed on Mar. 18, 2020.

(51) Int. Cl.
*A61K 35/60* (2006.01)
*A61K 9/00* (2006.01)
*A61K 47/22* (2006.01)

(52) U.S. Cl.
CPC .............. *A61K 35/60* (2013.01); *A61K 9/006* (2013.01); *A61K 47/22* (2013.01)

(58) Field of Classification Search
None
See application file for complete search history.

(56) References Cited

U.S. PATENT DOCUMENTS

| | | | |
|---|---|---|---|
| 4,002,775 A | 1/1977 | Kabara | |
| 4,513,008 A | 4/1985 | Revici et al. | |
| 5,952,392 A * | 9/1999 | Katz | A61K 31/20 514/936 |
| 9,072,714 B2 | 7/2015 | Loftsson et al. | |
| 2008/0138438 A1* | 6/2008 | Taylor | A01N 59/16 514/642 |
| 2012/0201911 A1* | 8/2012 | Cyr | A61K 36/9068 424/732 |

FOREIGN PATENT DOCUMENTS

| | | | | |
|---|---|---|---|---|
| CN | 101453888 A * | 6/2009 | ............. | A01N 31/02 |
| WO | 2017/077528 A2 | 5/2017 | | |

OTHER PUBLICATIONS

CN10453888A1—Google English Translation (Year: 2009).*
Fletcher et al., "A novel antiviral formulation inhibits a range of enveloped viruses," Journal of General Virology 2020; 101:1090-1102 (Year: 2020).*
Das et al., "Arachidonic acid and other unsaturated fatty acids and some of their metabolites function as endogenous antimicrobial molecules: A review", Journal of Advanced Research 11 (2018) 57-66. (Year: 2018).*
Hathaway III et al., "Omega 3 Fatty Acids and COVID-19: A Comprehensive Review", vol. 52, No. 4, pp. 478-495, Retrieved from the Internet: URL:https://www.ncbi.nlm.nih.gov/pmc/articles/PMC7779984/pdf/ic-52-478.pdf (Dec. 8, 2020).
Ilievska et al., "Topical Formulation Comprising Fatty Acid Extract from Cod Liver Oil: Development, Evaluation and Stability Studies", Marine Drugs, vol. 14, No. 6, 11 pages (2016).
Qing et al., "New evidence of SARS-CoV-2 transmission through the ocular surface", Graefe's Archive for Clinical Experimental Ophthalmology, vol. 259, pp. 1661-1662 (May 4, 2020).
Kristmundsdóttir et al., "Chapter 7: Lipids as Active Ingredients in Pharmaceuticals, Cosmetics and Health Foods", Lipids and Essential Oils as Antimicrobial Agents, pp. 151-177 (2011).
Desbois et al., "Antibacterial activity of long-chain polyunsaturated fatty acids against Propionibacterium acnes and *Staphylococcus aureus*", Marine Drugs, vol. 11, No. 11, pp. 4544-4557 (2013).
Jackman et al., "Review: Nanotechnology Formulations for Antibacterial Free Fatty Acids and Monoglycerides", Molecules vol. 21, No. 3, 19 pages (2016).
Kristinsson et al., "Nationwide Incidence and Outcomes of Patients With Coronavirus Disease 2019 Requiring Intensive Care in Iceland", Critical Care Medicine, vol. 48, No. 11, 4 pages (Aug. 18, 2020).
Yang et al., "The deadly coronaviruses: The 2003 SARS pandemic and the 2020 novel coronavirus epidemic in China", Journal of Autoimmunity, vol. 109, 17 pages (Mar. 30, 2020).
Thormar et al., "Inactivation of Visna Virus and Other Enveloped Viruses by Free Fatty Acids and Monoglycerides", Annals of the New York Academy of Sciences, vol. 724, pp. 465-471 (1994).
Hilmarsson et al., "Virucidal activities of medium- and long-chain fatty alcohols, fatty acids and monoglycerides against respiratory syncytial virus and parainfluenza virus type 2: Comparison at different pH levels", Archives of Virology, vol. 152, No. 12, pp. 2225-2236 (2007).
Isaacs et al., "Membrane-disruptive effect of human milk: inactivation of enveloped viruses", The Journal of Infectious Diseases, vol. 154, No. 6, pp. 966-971 (1986).
Das, "Arachidonic acid and other unsaturated fatty acids and some of their metabolites function as endogenous antimicrobial molecules: a review", Journal of Advanced Research, vol. 11, pp. 57-66 (2018).
International Search Report and Written Opinion of the International Searching Authority dated Aug. 18, 2021 for corresponding International Application No. PCT/IB2021/000189, 19 pages.
Thormar et al., "Antimicrobial lipids: Role in innate immunity and potential use in prevention and treatment of infections", Formatex, Retrieved from the Internet on Nov. 24, 2016: URL:http://www.formatex.info/microbiology4/vol3/1474-1488.pdf, pp. 1474-1488 (2013).

(Continued)

*Primary Examiner* — Kyung S Chang
(74) *Attorney, Agent, or Firm* — SHEPPARD, MULLIN, RICHTER & HAMPTON LLP

(57) ABSTRACT

An anti-viral composition or formulation is described that includes free fatty acids ("FFA"). Also described, are methods of making and using such a composition or formulation.

30 Claims, No Drawings

(56) References Cited

OTHER PUBLICATIONS

Thormar et al., "The role of microbicidal lipids in host defense against pathogens and their potential as therapeutic agents", Chemistry and Physics of Lipids, vol. 150, No. 1, pp. 1-11 (Oct. 11, 2007).
Khalil et al., "Broad beans (*Vicia faba*) and the potential to protect from COVID-19 coronavirus infection", vol. 20, No. 1, pp. 10-12, Retrieved from the Internet: URL:https://www.ncbi.nlm.nih.gov/pmc/articles/PMC7282436/pdf/sjp-20-10.pdf (2020).
Das, "Opinion: Can Bioactive Lipids Inactivate Coronavirus (COVID-19)?", Archives of Medical Research, vol. 51, No. 3, pp. 282-286 (Apr. 1, 2020).
Belluzzi et al., "Eicosapentaenoic free fatty acid to treat patients with SARS-Cov2 infection", Medical Hypotheses, vol. 143, 2 pages (retrieved on Jul. 12, 2020).

\* cited by examiner

FREE FATTY ACIDS AND METHODS OF MANUFACTURE AND USE FOR TREATING CORONAVIRUS AND OTHER VIRAL RESPIRATORY INFECTIONS

CROSS-REFERENCE TO RELATED APPLICATION

This application is a U.S. Non-Provisional Application, which claims the benefit of U.S. Provisional Application No. 62/991,368 filed on Mar. 18, 2020, and U.S. Provisional Application No. 63/073,757 filed on Sep. 2, 2020, the entire content of each is hereby incorporated by reference herein.

TECHNICAL FIELD

This application relates to compositions and formulations that comprise one or more free fatty acid ("FFA"). Such compositions can be in the form of a variety of compositions and/or formulations, including nasal and/or intraoral compositions or formulations. It also related to methods of making and using such compositions and formulations for treating bacterial, viral and fungal infections and/or preventing, minimizing and/or inhibiting the spread of such infections, including respiratory infections.

BACKGROUND

Various anti-viral compositions and formulations are known, but they are not optimal. There is an urgent need for safe and effective antiviral, and especially anti-coronavirus, compositions and/or formulations that can safely and effectively treat such infections and/or prevent, minimize, and/or inhibit the spread of such infections within and among populations. In particular, there is an urgent and global need for such compositions and/or formulations to treat respiratory infections such as those caused by, for example, Severe Acute Respiratory Syndrome Coronavirus 2 ("SARS-COV-2") and the resulting disease, COVID-19, and/or prevent, minimize, and/or inhibit the spread of such infections locally and globally. Furthermore, there is a continued need for compositions and/or formulations to prevent, minimize, and/or mitigate common viral respiratory infections, such as the common cold and the seasonal flu.

SUMMARY

Described herein is an antimicrobial formulation comprising an effective amount of an FFA extract to inhibit growth of a microbe. In exemplary embodiments, the effective amount of the FFA extract in the formulation is more than about 0.1% (v/v), and preferably from about 0.1% to about 20% (v/v). The concentration of the FFA extract when administered at the site of administration has a local concentration that is substantially constant for an effective period of time, preferably the local concentration of the FFA extract has a variation of less than about 2%. Preferred embodiments of the FFA extract concentration in the formulation and/or at the site of administration include at least about 0.1%, from about 0.1% to about 20% (v/v), from about 0.5% to about 20% (v/v), from about 1% to about 20% (v/v), from about 2% to about 20% (v/v), from about 1% to about 10%, from about 2% to about 10%, from about 1% to about 5% (v/v), from about 2% to about 5%, about 1% (v/v), about 1.5% (v/v), about 2% (v/v), and about 2.5% (v/v).

The FFA can contain one or more fatty acids exhibiting an antimicrobial activity for treatment of infections and/or for use as a prophylactic to prevent, substantially minimize and/or substantially inhibit microbial infections. One way in which the formulation achieves this is by reducing the number of viable microbes excreted by infected individuals, as well as reducing the viability of the microbes that may be received by a healthy individual.

An exemplary minimum effective period of time in which the antimicrobial formulation remains at the site of administration is at least about 1 second, about 5 seconds, about 10 seconds, about 20 seconds, about 30 seconds, about 1 minute, about 2 minutes, about 3 minutes, about 5 minutes, and about 10 minutes. The maximum effective period of time in which the antimicrobial formulation remains at the site of administration is the time before a significant side effect is observed. Exemplary side effects include irritation, discomfort, and intolerable repulsion. Exemplary maximum period of time is about 10 minutes to about 120 minutes, more preferably selected from the group consisting of about 10 minutes, about 30 minutes, about 60 minutes, about 90 minutes, and about 120 minutes.

In one embodiment, the microbe has a log reduction value ("LRV") when the same microbe is contacted by the formulation, and the LRV is comparable to the LRV observed when the microbe is contacted by of a solution of 35% (v/v) ethanol. In an exemplary embodiment, the LRV when the microbe contacted by the antiviral formulation is from about 1 to about 4, preferably from about 1.3 to about 4.0, more preferably from about 1.5 to about 4.0, more preferably from about 1.8 to about 4.0, more preferably from about 2.0 to about 4.0, more preferably from about 2.3 to about 4.0, more preferably from about 2.5 to about 4.0, more preferably from about 2.8 to about 4.0, more preferably from about 3.0 to about 4.0, more preferably from about 3.3 to about 4.0, more preferably from about 3.5 to about 4, and more preferably from about 3.8 to about 4.0. In another exemplary embodiment, the antiviral formulation inactivates and/or inhibits at least about 90% of the microbial replication, preferably from about 90.00% to about 99.99%, more preferably from about 94.99% to about 99.99%, more preferably from about 96.84% to about 99.99%, more preferably from about 98.42% to about 99.99%, more preferably from about 99.00% to about 99.99%, more preferably from about 99.50% to about 99.99%, more preferably from about 99.68% to about 99.99%, more preferably from about 99.84% to about 99.99%, more preferably from about 99.90% to about 99.99%, more preferably from about 99.95% to about 99.99%, more preferably from about 99.95% to about 99.99%, more preferably from about 99.97% to about 99.99%, and more preferably from about 99.98% to about 99.99%.

An exemplary FFA extract comprises one or more FFA is selected from the group consisting of palmitoleic acid, cis-vaccenic acid, oleic acid, gadoleic acid, gondoic acid, erucic acid, cetoleic acid, linoleic acid, α-linolenic acid, moroctic acid, eicosapentaenoic acid ("EPA"), docosahexaenoic acid ("DHA"), combinations thereof, and the like. An exemplary FFA extract includes one or more saturated or unsaturated fatty acids having a carbon chain that is from 4 to 36 carbons long (i.e., from C4 to C36). An exemplary FFA extract is derived from a marine organism, a fish, a fish-liver, a cod-liver, a cod-liver that is rich in omega-3 fatty acids, combinations thereof, and the like. An exemplary formulation the FFA extract is combined with a lipophilic solution such as an oil. An exemplary amount of the lipophilic solution in the antiviral formulation is at least 50%, preferably from about 80% to about 99.9%, from about 90% to about 99.9%, from about 95% to about 99.9%, from about 98% to about 99.9%, from about 99% to about 99.9%, from about 99.5% to about 99.9. The oil in the lipophilic solution is preferably derived from an marine organism, a fish oil, a fish-liver oil, a cod-liver oil, an oil rich in n-3 PUFAs, combinations thereof, and the like.

An exemplary formulation further comprises a flavoring agent such as a lemon flavor (I303). An exemplary formulation further comprises an antioxidant, such as a tocopherol. An exemplary formulation comprises an omega-3 FFA. Exemplary total omega-3 FFA is from about 320 to about 360 mg/g, wherein the total DHA FFA is preferably from about 100 to about 135 mg/g, and wherein the EPA FFA is preferably from about 150 to about 180 mg/g. An exemplary area percent of the DHA FFA is at least about 12%. Exemplary area percent of the EPA FFA is at least about 18%. An exemplary total amount of the FFA extract is from about 1.8% to about 2.5% (v/v). An exemplary formulation has an acid value is from about 2 to about 20 (mg KOH/g), more preferably from about 2.3 to about 15 (mg KOH/g), and more preferably from about 2.6 to about 5.0 (mg KOH/g). An exemplary formulation comprises a further step, wherein the further step is neutralization, bleaching, winterization, deodorization, purification by short path distillation, and any combinations thereof.

Also described herein is a method of treating a microbial infection, and/or preventing, substantially minimizing and/or substantially inhibiting the microbial infection, the method comprising administering to an individual subject in need thereof an effective dose of the antimicrobial formulation of this Application. Also described herein, is the antimicrobial formulation of this Application for use in treating a microbial infection in a subject; and/or as a prophylactic for preventing, substantially minimizing and/or substantially inhibiting a microbial infection in a subject. Also described herein is a use of the antimicrobial formulation of this Application in the preparation of a medicament for treating a microbial infection in a subject; and/or as a prophylactic for preventing, substantially minimizing and/or substantially inhibiting a microbial infection in a subject.

An exemplary microbe as used in this Application includes a bacteria, virus, fungus and any combinations thereof. An exemplary antimicrobial activity as used in this Application includes an antibacterial, antifungal, antiviral activity, and any combinations thereof. An Exemplary virus as used in this Application includes an encapsulated virus, a respiratory virus, a common cold virus, a flu virus, a coronavirus, a pneumovirus, a paramyxovirus, combinations thereof, and the like. An exemplary encapsulated virus as used in this Application includes a virus with a lipid envelope. An exemplary coronavirus includes a human coronavirus 229E ("hCoV-229E"), a SARS-COV, a MERS-COV, and a SARS-COV-2. An exemplary pneumovirus includes a respiratory syncytial virus ("RSV") and an exemplary paramyxovirus include a parainfluenza virus 3 ("PIV-3"). An exemplary flu virus includes an influenza A virus, influenza B virus, influenza C virus, and any other seasonal flu virus.

An exemplary formulation includes an oral and/or intraoral solution such as mouthwash solution, throat-wash solution, liquid-filled lozenge, liquid-filled tablet, liquid-filled capsule, beverage, syrup, gargle solution, mouth spray, throat spray, and nasopharynx spray; a nasal solution such as a nasal spray and nasal wash; an ocular solution such as an eye drop and eye wash; a topical medicine such as a facial mist and face wash; combinations thereof; and the like. The exemplary formulation can be administered to the mouth, nose, nasopharynx, eye, skin, and combinations thereof, to a subject in need thereof.

DETAILED DESCRIPTION

Interpretations and Definitions

Unless otherwise indicated, this description employs conventional chemical, biochemical, molecular biology, immunology and pharmacology methods and terms that have their ordinary meaning to persons of skill in this field (unless otherwise defined/described herein). All publications, references, patents and patent applications cited herein are hereby incorporated by reference in their entireties.

As used in this specification and the appended claims, the following general rules apply. Singular forms "a," "an" and "the" include plural references unless the content clearly indicates otherwise.

As used herein, the following terms shall have the specified meaning. The term "about" takes on its plain and ordinary meaning of "approximately" as a person of skill in the art would understand. Unless otherwise specified herein, "about" means±10%.

The term "substantially" means to some degree greater than if no composition or formulation, as described herein, were administered to the individual subject. In certain embodiments, "substantially" can mean, for example, a minimization and/or inhibition effect as compared to if no composition and/or formulation had been administered to the individual subject, wherein the minimization and/or inhibition effect is at least about 5%, at least about 10%, at least about 15%, at least about 20%, at least about 25%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% greater, and combinations and/or ranges thereof.

The term "comparable" means two values that are the same and/or has no substantial statistical differences. In certain embodiment, "comparable" with respect to LRV and percent reductions can mean the two values are, for example, within about ±30% of each other, within about ±20% of each other, within about ±10% of each other, within about ±5% of each other, within about ±2.5% of each other, within about ±1% of each other, within about ±0.5% of each other, within about ±0.25% of each other, within about ±0.1% of each other, and combinations and/or ranges thereof.

The term "comprise," "comprising," "contain," "containing," "include," "including," "include but not limited to," or "characterized by" is inclusive or open-ended and does not exclude additional, unrecited elements.

Existing and Emerging Respiratory Infectious Disease is a Growing Global Concern.

Respiratory disease has been a particular public health concern. The recent pandemic of the deadly and novel coronavirus SARS-COV-2, which causes COVID-19 in infected individuals, has infected more than 25 million people globally and took nearly 1 million lives as of August 2020. As of February 2021, the SARS-COV-2 and it variants have infected more than 113 million people globally and took more than 2.5 million lives. SARS-COV-2, like other coronaviruses, is believed to be transmitted by aerosol and water droplets. The majority of the viruses are transmitted from oral and nasopharynx fluids. However, there are also evidence of ocular transmission and replication of SARS-COV2 (see Qing et al. New evidence of SARS-COV-2 transmission through the ocular surface, *Graefes Arch Clin Exp Ophthalmol.* 2020 May 4: 1-2).

Coronaviruses ("CoVs") are spherical, enveloped, single-stranded linear positive-sense RNA viruses that belong to the order Nidovirales. They were first identified in mid-1960s and can broadly infect vertebrates including humans, birds, bats, cats, snakes, rodents, pigs, and other wild and domestic animals, all of which can be "subjects" in the present application. In addition to SARS-COV-2, six other human coronaviruses ("HCoVs" or "hCoVs") are currently known. They include the original SARS-COV, the MERS-COV, and four commonly detected hCoVs, 229E, OC43, NL63 and HKU1, which causes approximately 15% of all common colds (Y. Yang, F. Peng, R. Wang, K. Guan, T. Jiang, G. Xu, J. Sun, J. Chang, The deadly coronaviruses: The 2003 SARS pandemic and the 2020 novel coronavirus epidemic in China, Autoimmun. 2020 Mar. 3:102434). Other common upper respiratory pathogens include influenza virus, rhinovirus, parainfluenza virus ("PIV"), human metapneumovirus, rhinovirus/enterovirus ("RV"/"EV"), human bocavirus ("hBoV"), Group A Streptococci, Epstein-Barr virus ("EBV"), RSV, *Chlamydia pneumoniae/Mycoplasma pneumoniae, Legionella pneumophila*, and Group A Streptococci.

Fish Oil and Polyunsaturated Fatty Acids.

The health benefits of marine lipids containing polyunsaturated fatty acids ("PUFAs"), especially ω-3 polyunsaturated fatty acids ("n-3 PUFAs"), have been studied over the past several decades. In general, in vitro experiments and studies in animals have shown health benefits while studies in humans have sometimes given mixed results (D. M. Pereira, J. Vinholes, G. Correia-da-Silva, P. Valentao, N. Teixeira, P. B. Andrade, Fatty acids in marine organisms: In the pursuit of bioactive agents, Current Pharmaceutical Analysis, 7 (2011) 108-119; B. Ilievska, T. Loftsson, M. A. Hjalmarsdottir, G. M. Asgrimsdottir, Topical formulation comprising fatty acid extract from cod liver oil: development, evaluation and stability studies, Marine Drugs, 14(6) (2016); T. Loftsson, B. Ilievska, G. M. Asgrimsdottir, O. T. Ormarsson, E. Stefansson, Fatty acids from marine lipids: biological activity, formulation and stability of fatty acids from cod-liver oil, J. Drug Deliv. Sci. Technol., 34, 71-75 (2016)). It is believed that PUFAs can have beneficial effects against wide variety of diseases including cardiovascular diseases, psychiatric disorders, age-related macular degeneration, cancer, arthritis, colitis and pancreatitis, some of which are related to the anti-inflammatory effects of the long chain n-3 PUFAs. But PUFAs are known to possess other biological effects. For example, some PUFAs can have effects against a few bacteria, viruses and fungus (T. Kristmundsdóttir, S. Skúlason, Lipids as active ingredients in pharmaceuticals, cosmetics and health foods, in: H. Thormar (Ed.) Lipids and essential oils as antimicrobial agents, Wiley, Chichester, 2011, pp. 151-177; A. P. Desbois, K. C. Lawlor, Antibacterial activity of long-chain polyunsaturated fatty acids against *Propionibacterium acnes* and *Staphylococcus aureus*, Mar Drugs, 11 (2013) 4544-4557). These biological effects are frequently associated with specific PUFAs such as eicosapentaenoic acid ("EPA") and docosahexaenoic acid ("DHA"). The studies show that PUFAs can be used as enabling pharmaceutical excipients as well as active pharmaceutical ingredients. The impure fish-liver oil that was commonly consumed in Iceland in the late 1800s and the early 1900s was known to possess antimicrobial activity (GULL HAFSINS. HG Johnson and S Jonsdottir, Reykjavik 2008). However, it was puzzling that when highly-refined fish-liver oil began to replace the impure oil, the fish-liver oil appeared to lose its antimicrobial activity.

Free Fatty Acid (FFA).

A FFA is generally referred to as a nonesterified fatty acid. The fatty acid is "free" because a triglyceride has been hydrolyzed to release the nonesterified FFA from the glycerol. As used in this Application, FFA has the same meaning as one of ordinary skill would understand the term to mean. FFA can be extracted from oils and in particular fish oils with a varying amount of success.

We have surprisingly observed that FFA extract from cod-liver oil has significant antibacterial activity while the cod-liver oil itself, containing the same fatty acids in the form of triglycerides, did not affect bacterial growth (T. Loftsson, B. Ilievska, G. M. Asgrimsdottir, O. T. Ormarsson, E. Stefansson, Fatty acids from marine lipids: biological activity, formulation and stability of fatty acids from cod-liver oil, J. Drug Deliv. Sci. Technol., 34, 71-75 (2016)). Surprisingly, the fish-liver oil that was used in Iceland before the early 1900s contained significant amounts of FFA such as PUFAs, as well as partly hydrolyzed triglycerides (that is mono- and diesters of glycerol). We have discovered that by adding FFA, and/or monoglycerides, to the currently-marketed refined fish-liver oil, the oil becomes not only antibacterial, but also displays some antifungal and/or antiviral activity.

Method of Preparing a FFA Extract.

Preparation of the FFA mixture from fish oil has been described (T. Loftsson, E. Stefansson: Fatty acids for use as a medicament. U.S. Pat. No. 9,072,714B2, 7 Jul. 2015). The terms "FFA mixture" and "FFA extract" are used interchangeably in this Application. Whether the FFA solution is extracted from an oil, such as a fish oil, or mixed together from individual FFA compound(s), or a combination of these, the FFA solutions are all equally suitable for the formulation of this Application.

The FFA mixture is extracted from a fish oil (such as a fish-liver oil, for example cod-liver oil) after hydrolysis in an aqueous media. Sodium hydroxide (about 130 grams) is dissolved in a mixture of about 1.0 liter of ethanol and about 1.5 liter of purified water. Then about 1000 grams of cod-liver oil is added, and the mixture heated under reflux at about 85° C. for about 8 hours. After cooling to about 5° C., about 800 ml of about 6M hydrochloric acid is added and the oil phase separated from the aqueous solution. The oil is then washed four times with about 800 ml of purified water at about 50° C. and finally dried at room temperature under vacuum. The fatty acid composition of the extract and the cod-liver oil used to prepare the extract is determined by gas-chromatography. The relative FFA composition of the extract is approximately the same as in the unhydrolyzed oil (Table 1). Omega-3 fatty acids are a family of PUFAs that has a carbon-carbon double bond at the n-3 position, and includes notable members such as linolenic acid ("LNA") (including α-linolenic acid ("ALA", 18:3 ω-3), stearidonic acid ("SDA", 18:4 ω-3), eicosapentaenoic acid ("EPA", 20:5 ω-3), docosapentaenoic acid ("DPA"; 22:5 ω-3), and docosahexaenoic acid ("DHA", 22:6 ω-3). Cod-liver oil is a pale yellowish clear liquid that mainly consists of mixed triglycerides of saturated and unsaturated fatty acids, including long-chain n-3 PUFAs such as EPA and DHA. While vegetable oils such as corn oil may contain large amounts of linoleic acid (18:2 n-6), marine lipids such as cod-liver oil contain relatively high concentrations of EPA (20:5 n-3) and DHA (22:6 n-3), and are the major source of n-3 PUFAs.

Some fatty acids and their monoglycerides possess antimicrobial activities against certain bacteria, virus, or fungus (J. J. Kabara, R. Vrable, M. S. F. Lie Ken Jie, Antimicrobial lipids: natural and synthetic fatty acids and monoglycerides, Lipids, 12 (1977) 753-759; H. Thormar, Lipids and essential oils as antimicrobial agents, Wiley, Chichester, 2011). Furthermore, We have shown that both the fatty acid ("FA") extract from cod-liver oil and hydrophobic ointment containing the extract have a notable antiviral effect against a non-respiratory virus, herpes simplex virus type 1 ("HSV-1") (T. Loftsson, H. Thormar, J. H. Ólafsson, T. M. Gunnarsdóttir, B. Hjaltason, G. Gudmundsson, Fatty acid extract from cod-liver oil: activity against herpes simplex virus and enhancement of transdermal delivery of acyclovir in-vitro, Pharm Pharmacol. Commun., 4 (1998) 287-291). One percent FA extract caused a 50,000 fold or greater (≥4.7 log 10) reduction of non-respiratory viral infectivity in 10 min. Hydrophobic ointment containing 30% extract caused 1.5 million-fold (≥6.2 log 10) reduction of non-respiratory viral infectivity.

Thormar and co-workers have shown that lipids in fresh human milk do not inactivate viruses but become antiviral after storage of the milk for a few days at 4 or 23 degrees C. (C E Isaacs, H Thormar, T Pessolano, Membrane-disruptive effect of human milk: inactivation of enveloped viruses, J Infect Dis, 154 (6), 966-71, 1986; H. Thormar, C. E. Isaacs, K. S. Kim, H. R. Brown, Inactivation of visna virus and other enveloped virus is by FFA and monoglycerides, Ann. N. Y. Acad. Sci. 724, 465-471, 1994; H. Thormar, H. Hilmarsson, The role of microbicidal lipids in host defense against pathogens and their potential as therapeutic agents, Review Chem Phys Lipids, 150 (1), 1-11, 2007). The appearance of antiviral activity depends on active milk lipases and correlates with the release of FFA in the milk. They tested a number of fatty acids which are normal components of milk lipids against enveloped viruses, i.e., vesicular stomatitis virus, herpes simplex virus, and visna virus, and against a nonenveloped virus, poliovirus. Short-chain and long-chain saturated fatty acids were shown to have no or a very small antiviral effect at the highest concentrations tested. Medium-chain saturated and long-chain unsaturated fatty acids, on the other hand, were all highly active against the enveloped viruses tested. Monoglycerides of these fatty acids were also highly antiviral, in some instances at a concentration 10 times lower than that of the FFA. Furthermore, it has been suggested that intakes of α-linolenic and cis-linoleic acids, EPA and DHA might reduce the risk pneumonia (U. N. Das, Arachidonic acid and other unsaturated fatty acids and some of their metabolites function as endogenous antimicrobial molecules: a review, Review J Adv Res, 11, 57-66, 2018). Also, it has been shown that linear polyunsaturated acid can be applied topically to treat lesions associated with herpes infections (E. Revici, B, E. Sherwood; H. P. Benecke, J. M. Rice, R. W. Geisler, Virucidal compositions and therapy, U.S. Pat. No. 4,513,008, 23 Apr. 1985).

The application here relates to the discovery of the antiviral effects of FFA, including unsaturated FFA and its derivatives, especially with respect to certain respiratory viruses, including the SARS-COV-2 virus.

The FFAs and/or their derivatives and/or a combination thereof, when formulated with oil can be used to prevent, and/or substantially minimize and/or substantially inhibit and/or treat infections in the upper parts of the respiratory tract such as, for example, in the throat and nasopharynges of an individual human and/or animal subject in need thereof. In exemplary embodiments, the oil is derived from one or more marine sources and/or one or more vegetable sources. A marine source for the oil can include fish liver (such as cod liver and tuna liver), fish flesh or fish meal (such as fish flesh or fish meal from herring, apelin, mackerel, menhaden, sardine, anchovy, horse mackerel, blue whiting, and tuna), planktonic organisms, squid, crustaceans (i.e., krill), mollusks and any mixture thereof. A vegetable source for the oil can include safflower seed, corn, almond, sesame seed, soybean, linseed, rapeseed, grape seed, sunflower seed, wheat germ, hemp seed, and/or any combinations thereof and the like. In exemplary embodiments, the FFA and/or FFA derivatives can have a carbon chain length in the range of C4 to C36. In exemplary embodiments, the FFA can be an extract from cod-liver oil, the FFA extract contains saturated (e.g., myristic, palmitic and stearic acid), monounsaturated (palmitoleic, vaccenic, oleic, gondoic, gadoleic, erucic and cetoleic acid) and/or polyunsaturated (e.g., linoleic, moroctic, EPA and DHA acid) fatty acids. In exemplary embodiments, the unsaturated fatty acid can include palmitoleic acid, cis-vaccenic acid, oleic acid, gadoleic acid, gondoic acid, erucic acid, cetoleic acid, linoleic acid, α-linolenic acid, moroctic acid, EPA, DHA, and combinations thereof and the like. In exemplary embodiments, the FFA derivative can include FFA ethyl ester, monoglyceride (such as monocaprylin, monocaprin, monolaurin, monomyristin, monoolein and monolinolein glycerides), and/or a combination thereof. In exemplary embodiments, the formulation comprises at least about 20% (v/v) unsaturated FFA and at least about 5% (v/v) polyunsaturated FFA. In exemplary embodiments, the FFA is derived from one or more marine sources and/or one or more vegetable sources. A marine source for the oil can include fish liver (such as cod liver and tuna liver), fish flesh or fish meal (such as fish flesh or fish meal from herring, apelin, mackerel, menhaden, sardine, anchovy, horse mackerel, blue whiting, and tuna), planktonic organisms, squid, crustaceans (i.e., krill), mollusks, and any mixture thereof. A vegetable source for the oil can include safflower seed, corn, almond, sesame seed, soybean, linseed, rapeseed, grape seed, sunflower seed, wheat germ, hemp seed, and/or any combinations thereof and the like. In exemplary embodiments, the FFA and/or FFA derivatives can have a carbon chain length in the range of C4 to C36. In exemplary embodiments, the amount of FFA in the formulation is about 0.1% to about 20% (v/v). In other embodiments, the amount of the at least one FFA is selected from the group consisting of about 0.1%, about 0.5%, about 1%, about 1.5%, about 2%, about 2.5%, about 3%, about 3.5%, about 4%, about 4.5%, about 5%. About 5.5%, about 6%, about 6.5%, about 7%, about 7.5%, about 8%, about 8.5%, about 9%, about 9.5%, about 10%, about 10.5%, about 11% about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, about 20% (v/v) and combinations and/or ranges thereof. In exemplary embodiments, the subject being treated can be a human or a veterinary subject.

In exemplary embodiments, a composition and/or formulation is provided as an intraoral and/or nasal and/or nasal pharynx composition or formulation. Exemplary compositions or formulations can be prepared for topical administration including, for example, mouthwash formulations that can be formulated for swallowing, throat-wash formulations, gargle formulations, or sprays that can be readily applied to mouth and/or pharynges of an individual subject in need thereof. Exemplary formulations include a mouthwash, a throat wash, a liquid-filled lozenge, a liquid-filled tablet, a liquid-filled capsule, a beverage, a syrup, a gargle solution, a mouth spray, a throat spray, a nasal spray, and combinations thereof and the like.

In other exemplary embodiments, the composition may also be formulated into an eye drop and/or eye wash for ocular administration. In other exemplary embodiments, the composition may also be formulated into a face mist.

FFA Extract for Use in Treating and Preventing the Novel SARS-COV-2.

Applicant has surprisingly found that the formulations with FFA extract as described in this Application can be used to prevent, substantially minimize and/or substantially inhibit transmission and/or treat early infection of the novel SARS-COV-2, and that the formulations can prevent, substantially minimize, and/or substantially inhibit and/or treat early COVID-19, the disease caused by novel SARS-COV-2 infections.

Previously, there were some in vitro evidence that FFA can destroy a few encapsulated viruses such as RSV, PIV-2, HSV-1, visna virus, and vesicular stomatitis virus (Hilmarsson H, Traustason B S, Kristmundsdóttir T, Thormar H. Virucidal activities of medium- and long-chain fatty alcohols, fatty acids and monoglycerides against respiratory syncytial virus and parainfluenza virus type 2: Comparison at different pH levels. Arch. Virol. 152, 2225-2236, 2007; H Thormar, C E. Isaacs, K. S. Kim, H. R. Brown, Inactivation of visna virus and other enveloped viruses by FFA and monoglycerides, Ann N Y Acad Sci, 724, 465-71, 1994). There were also an animal study that suggest that the combination of FFA and its monoglyceride derivative reduces RSV in rats upon intranasal administration (H. Hilmarsson, T. Kristmundsdóttir, E. Gunnarsson, H. Thormar; J. Intranasal delivery of formulations containing virucidal lipid for treatment of respiratory syncytial virus (RSV) infection in rats. DRUG DEL. SCI. TECH., 23 (5) 455-457 2013). However, until now, it was not known whether a formulation comprising FFA extract and oil would be effective in humans against SARS-COV-2, the novel coronavirus first identified in Wuhan China in December 2019 that has since created a global pandemic (see Example 2).

It is important to point out that shortly following the discovery of the SARS-COV-2 and at the time of this Application, the virology of the novel SARS-COV-2 is largely unknown. The efficacy of drugs for treating and preventing the infection of this virus as well as the related therapeutic methods are still highly unpredictable. The field of SARS-CoV-2 is still in the process of emerging. Experimental studies are in largely infant stages and even skilled virologists have fundamental disagreements on the efficacy of treatments being used as well as being proposed. It is during this time of high uncertainty and unpredictability that Applicant has made the surprising discovery that FFA extract is an effective formulation against SARS-COV-2. Notably, Applicant has surprisingly discovered that the effectivity of the FFA extract is not limited to SARS-COV-2, but can extend to other viruses and microbes. Thus, Applicant's discovery opens the door to the attractive prospect of a broad-range antimicrobial.

In a preferred embodiment, the antiviral formulation of this Application comprises an effective amount of a FFA mixture. The effective amount of the FFA mixture in the antiviral formulation is at least about 0.1% (v/v) and is effective to inhibit growth of a virus in human subjects. The antiviral formulation is preferably lipophilic and the FFA mixture is preferably mixed with a lipophilic solution, such as an oil, preferably an oil derived from a marine source, a fish, a fish-liver, a cod-liver, combinations thereof, and the like. In one embodiment, the amount of the lipophilic solution in the antiviral formulation is at least 50%, preferably from about 80% to about 99.9%, from about 90% to about 99.9%, from about 95% to about 99.9%, from about 98% to about 99.9%, from about 99% to about 99.9%, from about 99.5% to about 99.9%.

In one embodiment, the human subject can have an active infection that is symptomatic or asymptomatic. In another embodiment, the human subject has not been infected but is at risk in acquiring an infection.

In one embodiment, the virus has a lipid envelope. In one embodiment, the virus is the SARS-COV-2. In a preferred embodiment, the antiviral formulation is also effective to inhibit growth of SARS-COV-2 and one or more other existing and emerging coronaviruses coronavirus such as SARS-COV, MERS-COV, HCOV-229E, HCoV-OC43, HCoV-NL63, HCOV-HKU1, and combinations thereof. In a preferred embodiment, the antiviral formulation is also effective to inhibit growth of SARS-COV-2 and one or more other respiratory virus, such as another existing or emerging coronavirus, flu virus (including an influenza A virus, influenza B virus, influenza C virus, and any other seasonal flu virus), pneumovirus (including a RSV), paramyxovirus (including a PIV-3); and/or one or more upper respiratory pathogen, such as a human metapneumovirus, RV/EV, hBoV, Group A Streptococci, EBV, *Chlamydia pneumoniae/Mycoplasma pneumoniae, Legionella pneumophila*, and Group A Streptococci; and combinations thereof.

The site of administration can be selected from the group consisting of mouth, nose, nasopharynx, eye, skin, and combinations thereof of an individual subject. The antiviral formulation can be in a form selected from the group consisting of a mouthwash solution, a throat wash solution, a liquid-filled lozenge, a liquid-filled tablet, a liquid-filled capsule, a beverage, a syrup, a gargle solution, a mouth spray, a throat spray, a nasal spray, eye drop, eye wash, facial mist, and combinations thereof and the like. Notably, Applicant has found that high risk individuals serving at the infectious disease ward of Landspítali University Hospital, ultimately did not develop COVID-19 when the individual's mouth and throat was washed and/or contacted periodically with a fish oil containing FFA (Example 2). It is worth noting here that the individuals participated in this study were truly in high risk because Landspítali University Hospital was only one of two hospitals in Iceland that has ICU capacity and was admitting COVID-19 patients (Kristinsson, Kristinsdottir, Blondal, Thormar, Kristjansson, Karason, Sigvaldason, Sigurdsson, Nationwide Incidence and Outcomes of Patients With Coronavirus Disease 2019 Requiring Intensive Care in Iceland, Crit Care Med. 2020 Aug. 18: 10.1097). Moreover, together, the two Icelandic hospitals admitted 27 patients to ICU as of Apr. 13, 2020, of which 4 patients ultimately passed away (Kristinsson, Kristinsdottir, Blondal, Thormar, Kristjansson, Karason, Sigvaldason, Sigurdsson, Nationwide Incidence and Outcomes of Patients With Coronavirus Disease 2019 Requiring Intensive Care in Iceland, Crit Care Med. 2020 Aug. 18: 10.1097).

In an exemplary embodiment, the antiviral formulation comprises an effective amount of 2.0% FFA extract in fish oil (Example 2). In an exemplary embodiment, for a period of time, from about 2 to 4 times a day, 5 mL of the antiviral formulation was used to wash and/or contact an individual's mouth and throat by gargling the antiviral formulation for about 15 to 30 sections (Example 1). The period of time administration can be about a week, from about 7 days to 14 days, and from about 7 days to as long as needed by the individual. In an exemplary embodiment, the antiviral formulation can be administered for about 2 times a day when the risk for infection is mild or moderate, and about 4 times a day when the risk of infection is more likely than not (Example 2). In an exemplary embodiment, the antiviral formulation, which comprises from about 1% to about 10% (v/v) FFA extract did not provide any severe irritation to the mouth and throat mucosa of the individual subject (Example 1). In another exemplary embodiment, the antiviral formulation, which comprises from about 1% to about 5% (v/v) FFA extract, did not provide any irritation to the mouth and throat. Additionally, the antiviral formulation did not require any additional flavoring agent to have an acceptable taste, although a flavoring agent can be added to improve the taste (Example 1). In particular, the antiviral formulation, which comprises from about 1%, or about 2%, or about 5% (v/v) FFA extract, was found to have acceptable tastes in the human subjects tested (see Example 1).

In a preferred embodiment, the FFA mixture was extracted from an oil source, such as from a fish oil, a marine organism, a fish-liver oil, a cod-liver oil, an oil rich in n-3 PUFAs, combinations thereof, and the like (Example 4). The FFA mixture can be hydrolyzed, neutralized, bleached, winterised and/or deodorized, and optionally purified by short path distillation (Example 4). In an exemplary embodiment, the FFA mixture comprises one or more FFA selected from Tables 1, 12 and 13. An exemplary FFA extract comprises Myristic acid (14:0), Palmitic acid (16:0), Stearic acid (18:0), Palmitoleic acid (16:1 n-7), cis-Vaccenic acid (18:1 n-7), Oleic acid (18:1 n-9), Gadoleic acid (20:1 n-11), Gondoic acid (20:1 n-9), Erucic acid (22:1 n-9), Cetoleic acid (22:1 n-11 (±13)), Linoleic acid (18:2 n-6), α-Linolenic acid (18:3 n-3), Moroctic acid (18:4 n-3), Eicosapentaenoic acid (EPA, 20:5 n-3), Docosahexaenoic acid (DHA, 22:6 n-3), combinations thereof, and the like. In another exemplary embodiment, the FFA mixture is selected from the group consisting of palmitoleic acid, cis-vaccenic acid, oleic acid, gadoleic acid, gondoic acid, erucic acid, cetoleic acid, linoleic acid, α-linolenic acid, moroctic acid, EPA, DHA, combinations thereof, and the like. In another exemplary embodiment, the FFA mixture comprises one or more saturated or unsaturated fatty acids with a carbon chain length in the range of from C4 to C36. In another embodiment, the FFA mixture can be derived from a marine organism, a fish oil, a fish-liver oil, a cod-liver oil, an oil rich in n-3 PUFAs, combinations thereof, and the like. In another embodiment, the FFA mixture can be combined with an oil derived from a marine organism, a fish oil, a fish-liver oil, a cod-liver oil, an oil rich in n-3 PUFAs, combinations thereof, and the like. Exemplary FFA extract compositions can be found at Tables 1, 12 and 13.

Applicant has further discovered that a FFA extract at concentrations from above 0.1% to about 20% FFA has antiviral effects (see Example 4). The FFA extract concentration is preferably from about 1% to about 2%. At this concentration, the FFA extract has low toxicity and causes minimal side effects (see Example 5). Applicant has further determined that the FFA extract at above 0.1% concentration can rapidly neutralize viruses at room temperature.

In an exemplary embodiment, the amount of the FFA extract in the antiviral formulation is selected from the group consisting of from about 0.1% to about 20% (v/v), from about 0.5% to about 20% (v/v), from about 1% to about 20% (v/v), from about 2% to about 20% (v/v), from about 1% to about 10%, from about 2% to about 10%, from about 1% to about 5% (v/v), and from about 2% to about 5% (v/v), about 1% (v/v), about 1.5% (v/v), about 2% (v/v), and about 2.5% (v/v). In another exemplary embodiment, the FFA extract when administered at a site of administration has a local concentration selected from the group consisting of from about 0.1% to about 20% (v/v), from about 0.5% to about 20% (v/v), from about 1% to about 20% (v/v), from about 2% to about 20% (v/v), from about 1% to about 10%, from about 2% to about 10%, from about 1% to about 5% (v/v), from about 2% to about 5% (v/v), about 1% (v/v), about 1.5% (v/v), about 2% (v/v), and about 2.5% (v/v). An exemplary formulation of the FFA extract and FFA extract in oil are provided in Examples 9 and 10 respectively. In an exemplary embodiment, the antiviral formulation comprises an extract from a fish oil, a flavoring agent (such as a lemon flavor 1303), and an antioxidant (such as a tocopherol), wherein the extract comprises a FFA mixture, the FFA mixture comprises one or more omega-3 FFA and, the amount of FFA mixture is from about 1% to about 10% (v/v). In another exemplary embodiment, the amount of the FFA mixture is from about 1.8% to about 2.5% (v/v), comprises from about 320 to about 360 mg/g total omega-3 fatty acids as FFA, comprises from about 100 to about 135 mg/g DHA as FFA, comprises from about 150 to about 180 mg/g EPA as FFA, comprises at least about 12 area percentage DHA, and/or comprises at least about 18 area percentage EPA.

Applicant has also surprisingly discovered that the acid value of the antiviral formulation is preferably from about 2.6 to 5.0 (mg KOH/g). It has been generally accepted that the acid value of fish oils should be limited to below 2 (mg KOH/g). Moreover, FFAs in fish oils have been generally considered as impurities. However, Applicant has discovered that antiviral activities are negligible in marine oils, such as fish oil and cod-liver oil, with acid value below 2 (mg KOH/g). In contrast, when the acid value is raised to more than 2 (mg KOH/g), significant antiviral activities are observed. In an exemplary embodiment, the acid value of the antiviral formulation comprising fish oil and FFA mixture is preferably from about 2 to about 20 (mg KOH/g), more preferably from about 2.3 to about 15 (mg KOH/g), and more preferably from about 2.6 to about 10 (mg KOH/g).

In an exemplary embodiment, the antiviral formulation further comprises an additional active ingredient selected from the group consisting of an antiviral, an antibiotic, an antifungal, and combinations thereof. Preferably the additional active ingredient is lipophilic. Exemplary antiviral active ingredient include rimantadine, amprenavir, atazanavir, indinavir, nelfinavir, saquinavir, tipranavir, abacavir, nevirapine, combinations thereof, and the like. Exemplary antibiotic active ingredient include tigecycline, ofloxacin, metronidazole, clarithromycin, clindamycin, chloramphenicol, rifampicin, isoniazid, combinations thereof, and the like. Exemplary antifungal active ingredient include isavuconazole, voriconazole, caspofungin, combinations thereof, and the like.

Applicant has discovered that the SARS-COV-2 and/or another virus when contacted by the antiviral formulation significantly increases the LRV of the SARS-COV-2 and/or another virus (see, for example, Examples 4, 6, and 7). In an exemplary embodiment, the antiviral formulation has a LRV that is comparable to an LRV observed when SARS-COV-2 and/or another virus is contacted by a solution of 35% (v/v) ethanol (see, example, Examples 6 and 7). In another exemplary embodiment, the SARS-COV-2 and/or another virus LRV when contacted by the antiviral formulation is from about 1 to about 4, preferably from about 1.3 to about 4.0, more preferably from about 1.5 to about 4.0, more preferably from about 1.8 to about 4.0, more preferably from about 2.0 to about 4.0, more preferably from about 2.3 to about 4.0, more preferably from about 2.5 to about 4.0, more preferably from about 2.8 to about 4.0, more preferably from about 3.0 to about 4.0, more preferably from about 3.3 to about 4.0, more preferably from about 3.5 to about 4, and more preferably from about 3.8 to about 4.0. In another preferred embodiment, the antiviral formulation inactivates and/or inhibits replication of the SARS-COV-2 and/or another virus by at least about 90%, preferably from about 90.00% to about 99.99%, more preferably from about 94.99% to about 99.99%, more preferably from about 96.84% to about 99.99%, more preferably from about 98.42% to about 99.99%, more preferably from about 99.00% to about 99.99%, more preferably from about 99.50% to about 99.99%, more preferably from about 99.68% to about 99.99%, more preferably from about 99.84% to about 99.99%, more preferably from about 99.90% to about 99.99%, more preferably from about 99.95% to about 99.99%, more preferably from about 99.95% to about 99.99%, more preferably from about 99.97% to about 99.99%, and more preferably from about 99.98% to about 99.99%.

In an exemplary embodiment, the antiviral formulation has a local concentration that is substantially constant for a minimal period of time at the site of administration and a maximum period of time at the site of administration. The minimum period of time can be from about 1 second to about 10 minutes. Examples of the minimum period of time can include about 1 second, about 5 seconds, about 10 seconds, about 20 seconds, about 30 seconds, about 1 minute, about 2 minutes, about 3 minutes, about 5 minutes, and about 10 minutes. The maximum period of time is a time before a significant side effect (such as an irritation) is observed. For example, the maximum period of time can be from about 10 minutes to about 120 minutes. Additional examples of the maximum period of time can include about 10 minutes, 30 minutes, 60 minutes, 90 minutes, and 120 minutes.

Applicant has also discovered that the antiviral formulation is surprisingly highly stable and retains high efficacy against SARS-COV-2 and/or another virus even when the original seal for the antiviral formulation was opened for a significant amount of time (Example 7). This is surprising because it is generally known that FFA extracts are prone to inactivation, oxidation and/or degradation, and thus unsuitable for hygienic routines. In an exemplary embodiment, the original seal of the antiviral formulation can be opened for at least 1 minute, from about 1 minute to about 21 days, from about half an hour to about 21 days, from about 1 hour to about 21 days, from about 3 hours to about 21 days, from about 6 hours to about 21 days, from about 9 hours to about 21 days, from about 12 hours to about 21 days, from about 15 hours to about 21 days, from about 18 hours to about 21 days, from about 21 hours to about 21 days, from about 24 hours to about 21 days, from about 2 days to about 21 days, from about 3 days to about 21 days, from about 4 days to about 21 days, from about 5 days to about 21 days, from about 6 days to about 21 days, from about 7 days to about 21 days, from about 10 days to about 21 days, from about 14 days to about 21 days, from about 16 days to about 21 days. In an embodiment, the SARS-COV-2 and/or another virus LRV when contacted by the antiviral formulation with a broken original seal has a LRV of at least 1, preferably at least 1.5. In an embodiment, the antiviral formulation with a broken original seal inactivates and/or inhibits replication of the SARS-COV-2 and/or another virus by at least about 90%, preferably from about 90.00% to about 99.99%, more preferably from about 94.99% to about 99.99%. In a preferred embodiment, the SARS-COV-2 and/or another virus LRV when contacted by the antiviral formulation with a broken original seal has a LRV of at least 1, preferably a LRV of from about 1 to about 4, more preferably from about 1.3 to about 4.0, more preferably from about 1.5 to about 4.0, more preferably from about 1.8 to about 4.0, more preferably from about 2.0 to about 4.0, more preferably from about 2.3 to about 4.0, more preferably from about 2.5 to about 4.0, more preferably from about 2.8 to about 4.0, more preferably from about 3.0 to about 4.0, more preferably from about 3.3 to about 4.0, more preferably from about 3.5 to about 4, and more preferably from about 3.8 to about 4.0. In an embodiment, the antiviral formulation with a broken original seal inactivates and/or inhibits replication of the SARS-COV-2 and/or another virus by at least about 90%, preferably from about 90.00% to about 99.99%, more preferably from about 94.99% to about 99.99%, more preferably from about 96.84% to about 99.99%, more preferably from about 98.42% to about 99.99%, more preferably from about 99.00% to about 99.99%, more preferably from about 99.50% to about 99.99%, more preferably from about 99.68% to about 99.99%, more preferably from about 99.84% to about 99.99%, more preferably from about 99.90% to about 99.99%, more preferably from about 99.95% to about 99.99%, more preferably from about 99.95% to about 99.99%, more preferably from about 99.97% to about 99.99%, and more preferably from about 99.98% to about 99.99%. The stability of the antiviral formulation combined with the strong efficacy of the antiviral formulation in reducing the SARS-COV-2 and/or another virus and in inactivating and/or inhibiting the replication of the SARS-COV-2 and/or another virus will be highly important in the storage, transportation, and self-administration of the antiviral formulation by the general public. The strong stability and at least 90% efficacy of the formulation allows for the formulation to be administered in multi-dose containers to be reused during the period of treatment and/or prevention. The strong stability and efficacy performance of the formulation will also be important in formulations in the form of, for example, mouth washes and nasal sprays, in which are not distributed in single use containers.

Also described herein, are methods of treating and/or preventing and/or minimizing and/or substantially inhibiting a disease caused by the SARS-COV-2 and/or another virus in an individual subject in need thereof, the method comprising administering to the subject the described antiviral formulation comprising an effective amount of a FFA mixture. In an exemplary embodiment, the method is effective in reducing the LRV value of the SARS-COV-2 and/or another virus by a substantial amount, including by an amount that is comparable to the LRV observed when the virus is contacted by a 35% ethanol solution. In another exemplary embodiment, the method is effective in inactivating and/or inhibiting the replication of the SARS-COV-2 and/or another virus by a substantial amount. The exemplary antiviral formulation can be in the form of a mouthwash solution, a throat wash solution, a liquid-filled lozenge, a liquid-filled tablet, a liquid-filled capsule, a beverage, a syrup, a gargle solution, a mouth spray, a throat spray, a nasal spray, eye drop, eye wash, facial mist, combinations thereof, and the like. The site of administration can be the mouth, nose, nasopharynx, eye, skin, and combinations thereof of an individual subject. In an exemplary embodiment, the method is effective in treating and/or preventing the respiratory disease from the SARS-COV-2 and/or another virus when the antiviral formulation is administered to the individual subject for a minimal period time of about 1 second, about 5 seconds, about 10 seconds, about 20 seconds, about 30 seconds, about 1 minute, about 2 minutes, about 3 minutes, about 5 minutes, and about 10 minutes; and a maximum period of time before a significant side effect (such as an irritation) is observed. The maximum time can be about 10 minutes to about 120 minutes, about 10 minutes, about 30 minutes, about 60 minutes, about 90 minutes, and about 120 minutes.

In exemplary embodiments, the described antiviral formulation can be used for treating and/or preventing a respiratory disease in a subject in need thereof. In exemplary embodiments, the antiviral formulation can also be used in the preparation of a medicament for treating and/or preventing a respiratory disease.

FFA Extract for Use in Treating and Preventing the Existing and Emerging Coronaviruses.

Applicant has also discovered that in an ongoing test, that human subjects did not develop COVID-19 while taking fish oils with FFA extract at 2.5% (see Examples 2 and 3). Since SARS-COV-2 settles in the mucosa of the upper respiratory tract (i.e., throat, pharynges and/or nasopharynges) for 3-7 days, the proposed formulation can prevent, substantially minimize and/or substantially inhibit viral transmission by destroying and/or disabling the virus during the first 1-7 days of viral contact (see Example 3). It will both reduce the number of viable viruses in the cough, sputum or sneeze of an infected individual and thus reduce probability of transmission; and reduce the probability of the survival and proliferation of a virus entering the upper respiratory tract of a person. Additionally, other Coronaviruses, such as SARS-COV, which causes SARS; MERS-COV, which causes Middle East respiratory syndrome (MERS); HCOV-229E, which causes the common cold; HCoV-OC43, which causes the common cold; HCoV-NL63 which causes the common cold; and HCoV-HKU1, which causes the common cold can be similarly treated, substantially minimized and/or substantially inhibited using the compositions and/or formulations described herein.

Applicant has discovered the antiviral formulation, use and methods disclosed in this Application are also effective at least against other existing coronaviruses, emerging coronaviruses, and combinations thereof. One example of the coronavirus is hCoV-229 (Table 9). In an exemplary embodiment, existing and emerging coronavirus include SARS-COV, MERS-COV, HCOV-229E, HCoV-OC43, HCOV-NL63, HCoV-HKU1.

FFA Extract for Use in Treating and Preventing Existing and Emerging Respiratory Microbial Infections.

Applicant has also discovered that the antiviral formulation, use and methods disclosed in this Application are also effective at least against other existing respiratory microbes, emerging respiratory microbes, and combinations thereof. The respiratory microbe can be a virus with a lipid envelope. Examples of the respiratory viruses include at least RSV (Table 6), influenza (Table 7), PIV (Table 8), hCoV-229 (Table 9). In an exemplary embodiment, existing and emerging respiratory viruses include a coronavirus such as SARS-COV, MERS-COV, HCOV-229E, HCoV-OC43, HCOV-NL63, HCoV-HKU1; a pneumovirus such as RSV; a paramyxovirus such as a PIV-3; a flu virus such as an influenza A virus, influenza B virus, influenza C virus, and any other seasonal flu virus. The existing and emerging respiratory microbes can also be a human metapneumovirus, RV/EV, hBoV, Group A Streptococci, EBV, *Chlamydia pneumoniae/Mycoplasma pneumoniae, Legionella pneumophila*, and Group A Streptococci.

Convenient Formulations can be Made.

Here, the FFA-fish oil solution as mouth and/or throat wash preparations and/or gargle or other intraoral solutions can access the virus and destroy and/or disable it on contact. Other exemplary formulations can include liquid-filled lozenges and/or oral tablets (including, for example, time-release coatings and/or layers and/or a liquid filled tablet and/or liquid-filled capsule), and/or toothpaste, and/or chewing gum, and/or beverages and/or syrups, and/or mouth spray, and/or throat spray, and/or nasal spray, and/or combinations thereof and the like. Each formulation includes an effective amount of one or more exemplary FFAs and/or compositions and/or formulations described herein. The formulation can interrupt and/or stop the transmission/infection and/or interrupt and/or stop the multiplication of the virus in the upper respiratory mucosa and/or make the systemic distribution (viremia and lung infection, pneumonia) and disease (COVID-19) by the virus less likely. The formulations and methods described herein can also be effective against respiratory syncytial virus (RSV), influenza A, influenza B, human metapneumovirus, rhinovirus/enterovirus (RV/EV), adenovirus, human bocavirus (hBoV), parainfluenza virus, *Chlamydia pneumoniae/Mycoplasma pneumoniae, Legionella pneumophila*, Group A Streptococci, EBV, combinations thereof, and the like.

The Antiviral Formulation can Exist in a Variety of Forms in the Presence of a Variety of Additives, Carriers, and Excipients.

Food grade flavors (such as lemon, cherry, or strawberry), coloring agents, extenders, diluents, fillers, among others, can be included in the formulation. The formulation may be in suspensions, pastes, solutions, syrups, jellies, creams and ointments, with or without conventional thickening agents such as carboxy methylcellulose, gelatins, among others. Likewise, sprays and mists can be prepared, including propellant and/or aerosol based sprays or mists. The formulation can also be present as a food additive as previously described, for example, in U.S. Pat. No. 4,002,775A.

One or more pharmaceutically acceptable carriers or excipients can be included in the formulation for use of oral delivery. Suitable formulations for use in the present invention are found in Remington's Pharmaceutical Sciences, Mack Publishing Company, Philadelphia, Pa., 17th ed. (1985).

The fatty acid and oil formulation can also be in the form of tablets, pills, powders, lozenges, elixirs, suspensions, emulsions, solutions, syrups, aerosols, gelatin capsules, and/or sterile liquids for intranasal administration (e.g., a spraying device). The supplements and formulations can also be formulated to provide rapid and/or sustained and/or delayed release of the fatty acid and oil to achieve for example a sufficient duration of administration to the individual subject in need to prevent, substantially minimize and/or substantially inhibit and/or treat a bacterial, viral and/or fungal infection, as described herein.

Liquid forms of the formulations include suspensions and/or emulsions. The formulations can be encapsulated, prepared as a colloid, introduced into the lumen of liposomes, and/or incorporated in the layers of liposomes. An exemplary liquid formulation can also consist of the oil itself, which can be encapsulated.

An exemplary formulation comprising oil and fatty acid can also be formulated into nanoparticles to take advantage of the potent anti-viral, anti-bacterial, and/or antifungal properties of the actives in superior delivery vehicles, such as nano-emulsions, liposomes, solid lipid nanoparticles, and controlled release hydrogels (A. Joshua A. B. Jackman, Y. Kyeong, L. Danlin, and C. Nam-Joon, Nanotechnology Formulations for Antibacterial Free Fatty Acids and Monoglycerides, Molecules 2016, 21(3), 305).

In exemplary embodiments, the compositions and/or formulations described herein can be used to reduce the risk of infection from infected individuals. FFA fish oil compositions and/or formulations described herein can also be used to reduce the number of viruses in sputum, cough or sneeze.

In exemplary embodiments, the compositions and/or formulations described herein can also reduce the risk of infection transmission. A person who gets a virus in the mouth, throat or nose can have a lower risk of the virus remaining undamaged and proliferating if FFA is administered to the mucosa. Ideally, in exemplary embodiments, the FFA is administered in an effective amount (as described herein) and also within an effective time frame including, for example, with 1-7 days of viral contact.

In exemplary embodiments, the compositions and/or formulations described herein can also reduce the likelihood of viruses growing in the pharynx and/or other upper respiratory regions following transmission. FFA can reduces the potential for viral survival, proliferation and/or spread in the pharyngeal mucosa using compositions and/or formulations, as described herein.

Efficacy of the Antimicrobial Formulation.

The efficacy of the antimicrobial formulation can be determined by any appropriate test or assay known by a person of ordinary skill in the art. For example, the efficacy can be determined in an in vitro, cell based assay by determining the LRV using one of the following two equations:

$$\text{Log Reduction Value} = \log_{10}(A/B) \quad (1)$$

$$\text{Log Reduction Value} = \log_{10}(A) - \log_{10}(B) \quad (2)$$

where,
- A is the number of viable microbe having contacted with the vehicle control, and
- B is the number of viable microbe having contacted with antimicrobial formulation. The vehicle control is the solution used to prepare and/or dilute the microbial, such as a test media and/or culture media. An exemplary vehicle control is MEM with 2% fetal bovine serum and 50 µg/mL gentamicin. In an exemplary embodiment, $\log_{10}(A)$ and $\log_{10}(B)$ are the microbial titer at each condition, which are also known as the log cell culture infectious dose or $\log_{50}\%$ end point ($\text{Log}_{10}\text{CCID}_{50}$ of the microbe per 0.1 mL of the microbe) for each condition. In another exemplary embodiment, the efficacy of the antimicrobial formulation can also be described in a percent reduction. An equation suitable for this purpose is:

$$\text{Percent Reduction} = (1 - 10^{-LRV}) \times 100\% \quad (3)$$

Examples 4 and 6-8 provide further exemplary methods to determine the efficacy, LRV and percent reduction of the antimicrobial formulation.

EXAMPLES

Example 1

Oil Containing FFA Extract are Well Tolerated in Human Subjects

The irritation and taste of fish oil containing FFA extract, with and without lemon was tested in five volunteers. The oil contained 1%, 2%, 5% or 10% (v/v) of the FFA extract in omega fish oil. Each subject poured 5 ml of the oil into the mouth and gargled for 15-30 seconds, in order to ensure that the oil can deal with and/or contact bacteria at the back of the tongue, the mouth and/or throat. Oils containing 1%, 2% and 5% (v/v) FFA were found to have acceptable taste by all subjects. The added lemon was generally found to improve the taste. No subject found these solutions to be irritating in the mouth or throat. Two subjects tested the oil containing 10% (v/v) FFA and both complained of mild to moderate irritation in throat and mouth mucosa.

Example 2

High Risk COVID-19 Subjects Did not Develop COVID-19 after Using the Formulation 30 volunteers were given 100 ml bottles each containing 2.0% FFA in fish oil and instructed to take 5 ml as mouth- and throat wash 2-4 times a day for 1 week. The solution should wash over and cover the mucosa in the mouth, throat/nasolarynges for at least several minutes as completely as possible. Subjects should not drink or eat for 15 minutes following application. The group included high risk personnel of the infectious disease ward in Landspítali University Hospital, where COVID-19 patients are taken care of. One patient with COVID-19 also received the solution. No subject complained of irritation or adverse effects from the FFA-fish oil. No subject developed COVID-19 while taking the solution. All subjects were pleased with the taste and texture of the solution.

Example 3

Example of Use

When an individual contracts a coronavirus SARS-COV-2, the virus is located to the mucosa of the throat, i.e., pharynges and/or nasopharynges, for 3-7 days. After this time, the virus can be detected in the blood (i.e., viremia) and/or the lungs. We propose that the virus is vulnerable to virucidal FFA-fish oil throat and/or mouth wash (or other, exemplary intraoral/throat compositions/formulations) in the first 1-7 days. The throat and/or mouth wash can also prevent, substantially minimize and/or substantially inhibit transmission, by destroying and/or disabling transmitted viruses as they enter the upper respiratory tract of an individual human or veterinary subject in need thereof.

The exemplary use of the FFA-fish oil mouthwash could be achieved in several ways:
1. A person who is likely to have acquired a coronavirus infection would use the FFA mouthwash and gargle in the throat about 4 times a day for about 7 days before viremia and/or lung infection takes place. The aim here is to prevent, substantially minimize and/or substantially inhibit the infection from becoming a systemic and/or lung disease and kill and/or disable the virus in the mucosa of the upper respiratory tract and/or pharynges.
2. A person at moderate or mild risk of coronavirus infection or simply wanting added protection from such infection could use the mouthwash regularly for example, for about 2 times a day or after a suspicion of transmission has occurred (public places, likely patient interaction, such as, for example, a cough and/or sneeze nearby).

TABLE 1

Relative amount of fatty acids in cod-liver oil and some vegetable oils. The oils consist mainly of mixed triglycerides where three fatty acids, of which at least two are different, are bonded via ester linkage to a glycerol backbone (T. Loftsson, B. Ilievska, G. M. Asgrimsdottir, O. T. Ornarsson, E. Stefansson, Fatty acids from marine lipids: biological activity, formulation and stability of fatty acids from cod-liver oil, J. Drug Deliv. Sci. Technol., 34, 71-75 (2016)).

| Trivial name of fatty acid (and nomenclature) | PhEur range for cod-liver oil (%) | Cod-liver oil (%) | Portuguese extra virgin olive oil (%) | Corn oil (%) | Fatty acid extract from codliver oil (%) |
|---|---|---|---|---|---|
| Saturated fatty acids (SFAs): | | | | | |
| Myristic acid (14:0) | 2.0-6.0 | 3.6 | — | — | 3.6 |
| Palmitic acid (16:0) | 7.0-14.0 | 10.5 | 11.3 | 11.6 | 10.4 |
| Stearic acid (18:0) | 1.0-4.0 | 2.6 | 3.3 | 1.8 | 2.6 |
| Mono-unsaturated fatty acids (MUFAs): | | | | | |
| Palmitoleic acid (16:1 n-7) | 4.5-11.5 | 6.5 | 1.0 | — | 6.5 |
| cis-Vaccenic acid (18:1 n-7) | 2.0-7.0 | 4.4 | — | — | 4.4 |
| Oleic acid (18:1 n-9) | 12.0-21.0 | 16.3 | 76.6 | 25.2 | 16.2 |
| Gadoleic acid (20:1 n-11) | 1.0-5.5 | 1.5 | — | — | 1.6 |
| Gondoic acid (20:1 n-9) | 5.0-17.0 | 9.6 | — | — | 9.4 |
| Erucic acid (22:1 n-9) | 0-1.5 | 0.6 | — | — | 0.6 |
| Cetoleic acid (22:1 n-11 (+13)) | 5.0-12.0 | 7.7 | — | — | 7.8 |
| Poly-unsaturated fatty acids (PUFAs): | | | | | |
| Linoleic acid (18:2 n-6) | 0.5-3.0 | 1.6 | 6.6 | 59.7 | 1.5 |
| α-Linolenic acid (18:3 n-3) | 0-2.0 | Not determined [a] | 0.6 | 0.8 | Not determined [a] |
| Moroctic acid (18:4 n-3) | 0.5-4.5 | 2.4 | — | — | 2.4 |
| Eicosapentaenoic acid (EPA) (20:5 n-3) [b] | 7.0-16.0 | 9.6 | — | — | 9.3 |
| Docosahexaenoic acid (DHA) (22:6 n-3) [c] | 6.0-18.0 | 12.5 | — | — | 11.9 |

[a] Not determined but cod-liver oil usually contains less than 1% α-linolenic acid.
[b] Timnodonic acid (PhEur)
[c] Cervonic acid (PhEur)

Example 4

FFA Neutralizes SARS-COV-2 In Vitro

FFAs extracted from fish-liver oil neutralizes SARS-COV-2 in vitro as compared to vehicle control (test media).

Cells and Viruses. Severe acute respiratory syndrome coronavirus 2 (SARS-CoV-2, USA-WA1/2020 strain) was obtained from the World Reference Center for Emerging Viruses and Arboviruses (WRCEVA) at the University of Texas Medical Branch (UTMB, Galveston, TX). A working stock was prepared prior to testing by passaging in primate cells (Vero 76 cells). Test media or culture media for prepared stock was MEM with 2% fetal bovine serum and 50 µg/mL gentamicin.

FFA extract preparation. FFA extract is prepared from fish oil has been prepared as previously described (T. Loftsson, E. Stefansson: Fatty acids for use as a medicament. U.S. Pat. No. 9,072,714B2, 7 Jul. 2015). The fatty acid mixture is extracted from fish oil (such as fish-liver oil, for example cod-liver oil) after hydrolysis in aqueous media. Sodium hydroxide (130 grams) is dissolved in a mixture of 1.0 liter of ethanol and 1.5 liter of purified water. Then 1000 grams of cod-liver oil is added, and the mixture heated under reflux at 85° C. for 8 hours. After cooling to 5° C. 800 ml of 6M hydrochloric acid is added and the oil phase separated from the aqueous solution. The oil is then washed four times with 800 ml of purified water at 50° C. and finally dried at room temperature under vacuum. The fatty acid composition of the extract and the cod-liver oil used to prepare the extract is determined by gas-chromatography. The relative fatty acid composition of the extract is approximately the same as in the unhydrolyzed oil (Table 1). Cod-liver oil is a pale yellowish clear liquid that mainly consists of mixed triglycerides of saturated and unsaturated fatty acids, including long-chain n-3 PUFAs such as EPA and DHA. While vegetable oils such as corn oil may contain large amounts of linoleic acid (18:2 n-6), marine lipids such as cod-liver oil contain relatively high concentrations of EPA (20:5 n-3) and DHA (22:6 n-3), and are the major source of n-3 PUFAs.

Neutralization/Virucidal Assay. A sample of the FFAs extract was pre-warmed in a 37° C. incubator, then dissolved 1 part in 1 part 100% ethanol. Test media was also pre-warmed in a 37° C. incubator to prepare compound dilutions of 4%, 2%, and 0.2%. Compound dilutions were added in six replicates to equal volume of SARS-COV-2 virus solution, to get final test concentrations of 2%, 1%, and 0.1%. Vehicle not containing compound was prepared as described above, substituting test media for the FFAs, and tested in parallel. Test media only was also tested for each prepared concentration to serve as toxicity controls.

Solution and virus were incubated at room temperature 10 minutes. The solution was then neutralized by 1/10 dilution in test media containing 10% FBS (fetal bovine serum). The entire assay was repeated as described above as an independent assay replicate on a separate day.

Virus Quantification Neutralized samples were pooled for virus quantification so that triplicate samples were combined for each test concentration. Since there were 6 replicates from each experiment for each FFA concentration, 3 each were combined into two pools for quantification, giving two replicates of data from each concentration.

Surviving virus was quantified by standard end-point dilution assay. Pooled samples were serially diluted 1/10 in test medium, then 100 µL of each dilution were plated into quadruplicate wells of 96-well plates containing 80-90% confluent Vero 76 cells. Plates were incubated at 37±2° C. with 5% $CO_2$ for 5 days. Each well was then scored for presence or absence of virus. The end-point titers ($CCID_{50}$) values were calculated using the Reed-Muench equation (Reed and Muench 1938). Vehicle controls were tested and the reduction of virus in test wells was compared to the vehicle controls to calculate as the log reduction value (LRV). Toxicity controls were tested with media not containing virus to observe if the samples were toxic to cells. Neutralization controls were tested to ensure that virus inactivation did not continue after the specified contact time, and that residual sample in the titer assay plates did not inhibit growth and detection of surviving virus. This was done by adding toxicity samples to titer test plates then spiking each well with a low amount of virus that would produce an observable amount of CPE during the incubation period. For statistical testing four total replicates of each concentration were tested and the mean and standard deviation were calculated. Test sample results were compared to vehicle controls by one-way ANOVA with Dunnett's multiple comparison tests using GraphPad Prism (version 8) software.

Here, we have shown for the first time, that FFAs from fish oil are effective in inactivating SARS-COV-2 upon contact (see Table 2). The effect is dose dependent, where 0.1% has no effect and 1% and 2% solutions are virucidal. The results show that FFAs extracted from fish-liver oil has an effective virucidal after a 10-minute incubation with SARS-COV-2 at room temperature, reducing virus from 4.2 log CCID50 per 0.1 mL in virus control samples to below the assay limit of detection (LRV>3.0, >99.9% of virus) when tested at 2% or 1% (P<0.0001, n=4). That is, 1% and 2% FFA significantly reduce SARS-COV-2 viral concentration more than 99.9% compared to vehicle control (p<0.0001). SARS-COV-2 titer was not reduced when 0.1% FFAs were tested (see Table 2).

TABLE 2

Virucidal efficacy of FFA extract against SARS-CoV-2 after a 10 minute incubation with virus at 22 ± 2° C.

| Compound | FFAs concentration | Virus Titer [a] | LRV [b] |
|---|---|---|---|
| FFA extract | 2% | 1.2 ± 0.6 * | 3.0 |
| FFA extract | 1% | 1.0 ± 0.5 * | 3.2 |
| FFA extract | 0.1% | 4.1 ± 0.3 | <1 |
| Vehicle Control | 0% | 4.2 ± 0.4 | — |

[a] $Log_{10}CCID_{50}$ of virus per 0.1 ml ($CCID_{50}$: cell culture infectious dose, 50% endpoint).
[b] LRV (log reduction value): reduction of virus compared to the vehicle control.
* P < 0.0001 (n = 4) by one-way ANOVA and Dunnett post-test compared with vehicle control.

For statistical analysis "<" signals were ignored.

Example 5

FFA are Generally Tolerable with Minimal Side Effects

The FFAs extracted from cod-liver oil showed some cytotoxicity in Vero 76 cells, affecting ability to detect virus CPE in cells and altering the limit of detection in one of the two assay replicates. Consequently, the limit of detection was either 0.7 or 1.7 log CCID50 per 0.1 mL in the 2% and 1% test samples. If virus was below the limit of detection, "<" signs were ignored for statistical analysis, and therefore LRV values are conservative.

Survey. In the human study 49 volunteers who had used the marketed food additive containing 2% FFAs in cod liver oil (lemon extract added for taste; Lýsi hf. Reykjavik, Iceland) were asked to answer a survey. 42 answered the questionnaire, 29 men and 18 women, age 22-70 years. They had used the marketed food additive as mouth- and throat-wash, one teaspoon (5 ml) 2 or 4 times a day for 10 days.

Of the 42 participants who answered the questionnaire survey and had used the food additive, none reported serious adverse events. Ten individuals reported minor irritation or dryness in the throat and/or mild discomfort in the stomach after ingestion.

1% FFA in cod liver oil is listed in the European Pharmacopoeia and 2% FFA in cod liver oil is well tolerated as a marketed food additive in Iceland. This opens the way for development and testing of using FFAs to fight SARS-COV-2 and other enveloped viruses and reduce their transmission.

One possible approach is to wash the mouth and throat with fish oil containing FFAs in order to reduce viability of viruses in the saliva and on the mucosa. 1 and 2% FFA inactivate SARS-COV-2 in vitro and are well tolerated in cod liver oil as mouth wash. Widely available in industrial quantities, FFA in fish oil may have potential as mouth/throat wash to reduce concentration of SARS-COV-2 viruses in saliva and upper respiratory mucosa and reduce transmission.

Example 6

The SARS-COV-2 Viral Inactivation Efficacy of a FFA Extract is Comparable to 35% Ethanol Virus, media and cells were prepared as in Example 4.

Neutralization/Virucidal Assay. A sample of FFA extract is received from the sponsor and is sealed and unopened until the day of testing. The FFA extract, test media, and vehicle not containing compound are pre-warmed, prepared and diluted as in Example 4. Compound dilutions are added in six replicates as in Example 4. Test media serving as toxicity controls are also prepared as in Example 4. Ethanol is tested in as a positive control and water only as a virus control. Solution and virus are incubated and then neutralized as in Example 4.

Virus Quantification. Neutralized samples are pooled for virus quantification so that triplicate samples are combined for each test concentration. Since there were 6 replicates of each FFA extract concentration, 3 were combined into two pools for quantification, giving two replicates of data for each test concentration. Surviving virus are quantified by standard end-point dilution assay. Pooled samples are serially diluted and plated into quadruplicate wells of 96-well plates containing 80-90% confluent Vero 76 cells as in Example 4. Plates are incubated, results are scored, and the CCID50 values are as in Example 4.

Controls. Virus controls are tested in water and the reduction of virus in test wells compared to virus controls are calculated as LRV. Toxicity controls and neutralization controls are tested as in Example 4.

Results. Virus titers and LRV for FFA extract against SARS-COV-2 are shown in Table 3. Full cytotoxicity are observed in the highest dilution (1/10) of the 2% samples and therefore the limit of detection was 1.7 log CCID50 per 0.1 mL. Significant cytotoxicity are also observed in one replicate of the 1% sample affecting the detection of virus (limit of detection=1.7 log CCID50 per 0.1 mL). The second replicate of the 1% sample exhibited less cytotoxicity and virus is detectable in those wells (limit of detection=0.7 log CCID50 per 0.1 mL). This may be due to diluting the fatty compound in aqueous solutions, which may be somewhat inconsistent and lead to some pipetting variability.

To determine LRV, all samples are compared to the virus control sample, which had 4.0 log CCID50 per 0.1 mL of virus. When tested at 2% FFA extract was an effective virucidal after a 10-minute incubation with SARS-COV-2 at room temperature, reducing virus from below the limit of detection of 1.7 log CCID50 per 0.1 mL (LRV>2.3, >99%). Similarly, when tested at 1%, virus is reduced below the limit of detection of (LRV>2.3, >99% or LRV>3.3, >99.9%). Virus is not reduced by ≥1 log CCID50 when FFA extract are tested at 0.1%.

Neutralization controls demonstrated that residual sample do not inhibit virus growth and detection in the endpoint titer assays in wells that do not have cytotoxicity. The positive control performed as expected.

TABLE 3

Virucidal efficacy of FFA extract against SARS-CoV-2 after a 10 minute incubation with virus at 22 ± 2° C.

| Compound | FFAs concentration | Virus Titer [a] | LRV [b] |
|---|---|---|---|
| FFA extract | 2% | <1.7 | >2.3 |
| FFA extract | 2% | <1.7 | >2.3 |
| FFA extract | 1% | <0.7 | >3.3 |
| FFA extract | 1% | <1.7 | >2.3 |
| FFA extract | 0.1% | 4.0 | 0 |
| FFA extract | 0.1% | 4.0 | 0 |
| Vehicle Control | 0% | 4.0 | 0 |
| Vehicle Control | 0% | 4.5 | 0 |
| Ethanol | 35% | <0.7 | >3.3– |
| Virus Control | n/a | 4.0 | — |

[a] $Log_{10}CCID_{50}$ of virus per 0.1 ml.
[b] LRV (log reduction value): reduction of virus compared to the vehicle control.

Example 7

Unsealed FFA Extract Also have Some Detectable SARS-CoV-2 Viral Inactivation

Virus, media, cells and controls are prepared as in Example 6. Virucidal Assay is prepared as in Example 6 with the addition of a second independent replicate 16 days after the sealed FFA extract sample is opened. This second independent replicate is performed in triplicate rather than six replicates. Virus quantification is generally performed as in Example 6. Since there were 6 replicates of each FFA extract concentration, 3 were combined into two pools for quantification, giving two sets of data for each test concentration for assay replicate 1 and one set of data for assay replicate 2.

Results. Virus titers and LRV for FFA extract against SARS-COV-2 are shown in Table 4. Some cytotoxicity in Vero 76 cells are observed in the highest dilution (1/10) of FFA extract at all test concentrations, but the toxicity do not affect detection of virus in those wells.

In assay replicate 1, when tested at 2%, FFA extract was an effective virucidal after a 10-minute incubation with SARS-COV-2 at room temperature, reducing virus from 4.3 to <0.7 log CCID50 per 0.1 mL (>99.9%) in both sample pools. Further, at 1% FFA extract demonstrated virucidal activity reducing virus to <0.7 and 1 log CCID50 per 0.1 mL in the two sample pools, respectively (>99.9%). Virus is not reduced by ≥1 log CCID50 when FFA extract are tested at 0.1%.

When retested in an independent replicate (assay replicate 2), the FFA extract sample reduces SARS-COV-2 by from 4.0 to 2.5 log CCID50 per well in both the 2% and 1% sample (96%). Virus is not reduced in the 0.1% sample. Where the compound is unsealed following assay replicate 1, there may have been some deterioration of the compound leading to reduced virucidal activity.

Like the results in Table 3, neutralization controls demonstrated that residual sample do not inhibit virus growth and detection in the endpoint titer assays in wells that did not have cytotoxicity. The positive control performed is as expected.

TABLE 4

Virucidal efficacy of FFA extract against SARS-CoV-2 after a 10 minute incubation with virus at 22 ± 2° C.

| Compound | FFAs concentration | Assay Replicate | Virus Titer [a] | LRV [b] |
|---|---|---|---|---|
| FFA extract | 2% | 1 | <0.7 | >3.6 |
| FFA extract | 2% | 1 | <0.7 | >3.6 |
| FFA extract | 2% | 2 | 2.5 | 1.5 |
| FFA extract | 1% | 1 | <0.7 | >3.6 |
| FFA extract | 1% | 1 | 1.0 | 3.3 |
| FFA extract | 1% | 2 | 2.5 | 1.5 |
| FFA extract | 0.1% | 1 | 3.7 | 0.6 |
| FFA extract | 0.1% | 1 | 4.5 | 0 |
| FFA extract | 0.1% | 2 | 4.0 | 0 |
| Vehicle Control | 0% | 1 | 3.7 | 0.6 |
| Vehicle Control | 0% | 1 | 4.5 | 0 |
| Vehicle Control | 0% | 2 | 4.0 | 0 |
| Ethanol | 35% | 1 | <0.7 | >3.6– |
| Ethanol | 35% | 2 | <0.7 | >3.3 |
| Virus Control | n/a | 1 | 4.3 | — |
| Virus Control | n/a | 2 | 4.3 | — |

[a] $Log_{10}CCID_{50}$ of virus per 0.1 ml
[b] LRV (log reduction value): reduction of virus compared to the vehicle control.

Example 8

Low Concentrations of FFA Extract can Neutralize Other Enveloped Respiratory Viruses Virus, media and cells. Virus stocks are prepared prior to testing by growing in cell culture according to Table 5. SARS-COV-2, USA-WA1/2020 strain, virus stock is prepared prior to testing by passaging in Vero 76 cells. Culture media for prepared stock (test media) is MEM with 2% fetal bovine serum and 50 μg/mL gentamicin.

Neutralization/Virucidal Assay. A sample of FFA extract is received from the sponsor and is sealed and unopened until the day of testing. Compound is pre-warmed in a 37° C. incubator, then dissolved 1 part in 1 part 100% ethanol. Test media is also pre-warmed in a 37° C. incubator to prepare compound dilutions of 2%, 1%, and 0.1%. Compound dilutions are added to triplicate tubes and virus stock solution is added so that there is 10% virus solution and 90% sample by volume. Vehicle not containing test sample is prepared as described above and tested in parallel. Test media only is tested for each prepared concentration to serve as toxicity controls. Ethanol is tested as a positive control and water only as a negative virus control. Solution and virus are incubated at room temperature 10 minutes. The solution is then neutralized by 1/10 dilution in test media containing.

Virus Quantification. Neutralized samples are pooled for virus quantification so that triplicate samples are combined for each test concentration. Surviving virus is quantified by standard end-point dilution assay in cells as indicated in Table 1. Plates are incubated at 37±2° C., or 33±2° C. for HRV, with 5% CO2 for 5 days. Each well is then scored for presence or absence of virus. The end-point titers (CCID50) values are calculated using the Reed-Muench (1948) equation.

Controls. Virus controls are tested in water and the reduction of virus in test wells compared to virus controls is calculated as the LRV. Toxicity controls are tested with media not containing virus to see if the samples are toxic to cells. Neutralization controls are tested to ensure that virus inactivation do not continue after the specified contact time, and that residual sample in the titer assay plates do not inhibit growth and detection of surviving virus. This is done by adding toxicity samples to titer test plates then spiking each well with a low amount of virus that will produce an observable amount of CPE during the incubation period.

Results. Virus titers and LRV for FFA extract against a panel of respiratory viruses are shown in Tables 6-11. To determine LRV, all samples are compared to the virus control sample. Samples with <1 log reduction of virus are not considered active for virucidal activity. The limit of detection of virus in the endpoint assay is 0.7 log CCID50 per 0.1 mL. In some cases, the virus input and amount of virus recovered in the virus control wells is ≤3.0 log CCID50 (less than 1,000 CCID50), limiting the amount of virus reduction that can be observed.

When tested at 2% FFA extract exhibited virucidal activity after a 10-minute incubation with three enveloped viruses, RSV (LRV=2.0), PIV-3 (LRV=1.3), and hCov-229E (LRV=1.0), though it does not reduce any of the viruses below the limit of detection. It performed similarly at 1% against RSV (LRV=1.5). It does not reduce virus titer by ≥1 log at other concentrations against these viruses.

FFA extract also demonstrated inconsistent activity against influenza virus (enveloped), reducing virus by 1 log (LRV=1) in the 1% and 0.1% samples but not the 2% sample. It is not effective against Ad-5 or HRV-14, the two non-enveloped viruses tested in the panel.

Neutralization controls demonstrated that residual sample does not inhibit virus growth and detection in the endpoint titer assays in wells that do not have cytotoxicity. Ethanol performed as expected though less effective against non-enveloped viruses and it does not reduce HRV-14 by >1 log.

TABLE 5

Virus stocks preparation details.

| Virus[a] | Detail | Cell Type | Culture Media[b] |
|---|---|---|---|
| RSV | A2 | MA-104 | MEM 5% FBS |
| Flu A(H1N1) | A/CA/09/07 | MDCK | <0.7 MEM, 10 U/mL Trypsin, 1 μg/mL EDTA |
| PIV-3 | 14702 | MA-104 | MEM 5% FBS |
| hCoV | 229E(alpha) | Huh7 | MEM 5% FBS |
| HRV-14 | 14 | HeLa | MEM 5% FBS, 25 mM $MgCl_2$ |
| Adenovirus | Type 5 | A549 | DMEM 2% FBS |

[a]RSV: respiratory syncytial virus; Flu A(H1N1): influenza A(H1N1)pdm09; PIV-3: parainfluenza virus type 3; hCoV: human coronavirus; HRV: human rhinovirus.
[b]All media also contain 50 μg/mL gentamicin.

TABLE 6

Virucidal activity of FFA extract against RSV after incubation with virus at 22 ± 2° C.

| Compound | Concentration | Contact Time | Toxicity[a] | Neut. Control[b] | Virus Titer[c] | VC Titer[c] | LRV[d] |
|---|---|---|---|---|---|---|---|
| FFA extract | 2% | 10-min | None | None | 1.0 | 3.0 | 2.0 |
| FFA extract | 1% | 10-min | None | None | 1.5 | 3.0 | 1.5 |
| FFA extract | 0.1% | 10-min | None | None | 2.3 | 3.0 | 0.7 |
| Vehicle | 0% | 10-min | None | None | 3.0 | 3.0 | 0 |
| Ethanol | 70% | 10-min | None | None | 1.0 | 3.0 | 2.0 |

[a]Cytotoxocity indicates the highest dilution of the endpoint titer where full (80-100%) cytotoxicity was observed.
[b]Neutralization control indicates the highest dilution of the endpoint titer where compound inhibited virus CPE in wells after neutralization (ignored for calculation of virus titer and LRV).
[c]Virus titer of test sample or virus control (VC) in log10 CCID50 of virus per 0.1 mL.
[d]LRV (log reduction value) is the reduction of virus in test sample compared to the virus control.

TABLE 7

Virucidal activity of FFA extract against Influenza(H1N1)pdm09 virus after incubation with virus at 22 ± 2° C.

| Compound | Concentration | Contact Time | Toxicity[a] | Neut. Control[b] | Virus Titer[c] | VC Titer[c] | LRV[d] |
|---|---|---|---|---|---|---|---|
| FFA extract | 2% | 10-min | None | None | 6.3 | 7.0 | 0.7 |
| FFA extract | 1% | 10-min | None | None | 6.0 | 7.0 | 1.0 |
| FFA extract | 0.1% | 10-min | None | None | 6.0 | 7.0 | 1.0 |
| Vehicle | 0% | 10-min | None | None | 6.7 | 7.0 | 0.3 |
| Ethanol | 70% | 10-min | None | None | 3.0 | 7.0 | 4.0 |

[a]Cytotoxocity indicates the highest dilution of the endpoint titer where full (80-100%) cytotoxicity was observed.
[b]Neutralization control indicates the highest dilution of the endpoint titer where compound inhibited virus CPE in wells after neutralization (ignored for calculation of virus titer and LRV).
[c]Virus titer of test sample or virus control (VC) in log10 CCID50 of virus per 0.1 mL.
[d]LRV (log reduction value) is the reduction of virus in test sample compared to the virus control.

TABLE 8

Virucidal activity of FFA extract against PIV-3 after incubation with virus at 22 ± 2° C.

| Compound | Concentration | Contact Time | Toxicity[a] | Neut. Control[b] | Virus Titer[c] | VC Titer[c] | LRV[d] |
|---|---|---|---|---|---|---|---|
| FFA extract | 2% | 10-min | None | None | 1.7 | 3.0 | 1.3 |
| FFA extract | 1% | 10-min | None | None | 2.7 | 3.0 | 0.3 |
| FFA extract | 0.1% | 10-min | None | None | 3.3 | 3.0 | 0 |
| Vehicle | 0% | 10-min | None | None | 3.0 | 3.0 | 0 |
| Ethanol | 70% | 10-min | None | None | <0.7 | 3.0 | >2.3 |

[a]Cytotoxocity indicates the highest dilution of the endpoint titer where full (80-100%) cytotoxicity was observed.
[b]Neutralization control indicates the highest dilution of the endpoint titer where compound inhibited virus CPE in wells after neutralization (ignored for calculation of virus titer and LRV).
[c]Virus titer of test sample or virus control (VC) in log10 CCID50 of virus per 0.1 mL.
[d]LRV (log reduction value) is the reduction of virus in test sample compared to the virus control.

TABLE 9

Virucidal activity of FFA extract against hCoV-229E after incubation with virus at 22 ± 2° C.

| Compound | Concentration | Contact Time | Toxicity[a] | Neut. Control[b] | Virus Titer[c] | VC Titer[c] | LRV[d] |
|---|---|---|---|---|---|---|---|
| FFA extract | 2% | 10-min | None | None | 1.7 | 2.7 | 1.0 |
| FFA extract | 1% | 10-min | None | None | 2.5 | 2.7 | 0.2 |
| FFA extract | 0.1% | 10-min | None | None | 3.0 | 2.7 | 0 |
| Vehicle | 0% | 10-min | None | None | 2.5 | 2.7 | 0.2 |
| Ethanol | 70% | 10-min | None | None | <0.7 | 2.7 | >2.0 |

[a]Cytotoxocity indicates the highest dilution of the endpoint titer where full (80-100%) cytotoxicity was observed.
[b]Neutralization control indicates the highest dilution of the endpoint titer where compound inhibited virus CPE in wells after neutralization (ignored for calculation of virus titer and LRV).
[c]Virus titer of test sample or virus control (VC) in log10 CCID50 of virus per 0.1 mL.
[d]LRV (log reduction value) is the reduction of virus in test sample compared to the virus control.

TABLE 10

Virucidal activity of FFA extract against HRV-14 after incubation with virus at 22 ± 2°C.

| Compound | Concentration | Contact Time | Toxicity[a] | Neut. Control[b] | Virus Titer[c] | VC Titer[c] | LRV[d] |
|---|---|---|---|---|---|---|---|
| FFA extract | 2% | 10-min | None | None | 4.7 | 5.3 | 0.6 |
| FFA extract | 1% | 10-min | None | None | 5.5 | 5.3 | 0 |
| FFA extract | 0.1% | 10-min | None | None | 5.0 | 5.3 | 0.3 |
| Vehicle | 0% | 10-min | None | None | 5.5 | 5.3 | 0 |
| Ethanol | 70% | 10-min | None | None | 4.5 | 5.3 | 0.8 |

[a]Cytotoxocity indicates the highest dilution of the endpoint titer where full (80-100%) cytotoxicity was observed.
[b]Neutralization control indicates the highest dilution of the endpoint titer where compound inhibited virus CPE in wells after neutralization (ignored for calculation of virus titer and LRV).
[c]Virus titer of test sample or virus control (VC) in log10 CCID50 of virus per 0.1 mL.
[d]LRV (log reduction value) is the reduction of virus in test sample compared to the virus control.

TABLE 11

Virucidal activity of FFA extract against Ad-5 after incubation with virus at 22 ± 2° C.

| Compound | Concentration | Contact Time | Toxicity[a] | Neut. Control[b] | Virus Titer[c] | VC Titer[c] | LRV[d] |
|---|---|---|---|---|---|---|---|
| FFA extract | 2% | 10-min | None | None | 5.7 | 5.7 | 0 |
| FFA extract | 1% | 10-min | None | None | 5.7 | 5.7 | 0 |
| FFA extract | 0.1% | 10-min | None | None | 5.3 | 5.7 | 0.4 |
| Vehicle | 0% | 10-min | None | None | 5.7 | 5.7 | 0 |
| Ethanol | 70% | 10-min | None | None | 5.3 | 5.7 | 3.4 |

[a]Cytotoxocity indicates the highest dilution of the endpoint titer where full (80-100%) cytotoxicity was observed.
[b]Neutralization control indicates the highest dilution of the endpoint titer where compound inhibited virus CPE in wells after neutralization (ignored for calculation of virus titer and LRV).
[c]Virus titer of test sample or virus control (VC) in log10 CCID50 of virus per 0.1 mL.
[d]LRV (log reduction value) is the reduction of virus in test sample compared to the virus control.

Example 9

Exemplary Formulation of a FFA Extract

A dark-brown solid fat processed from fully refined fish oil containing high amounts of omega-3 fatty acids, wherein the oil is hydrolysed, washed, and dried. The oil is stable at or below 25° C. for 12 months in sealed original containers without exposure to direct sunlight. An exemplary formulation is shown in Table 12.

TABLE 12

An exemplary formulation of a FFA extract.

| Analytical parameters: | Specification |
|---|---|
| Free fatty acids (%) | min. 95 |
| Moisture(%) | max 1.0 |
| Eicosapentaenoic acid (EPA) (mg/g as FFA) | min. 150 |
| Docosahexaenoic acid (DHA) (mg/g as FFA) | min. 100 |
| Full fatty acids profile (area%) | as analysed |
| Color (Gardner units) | max 12.0 |
| Peroxide value (meq. $O_2$/kg) | max 10.0 |

Example 10

Exemplary Formulation of a FFA Extract in Fish Oil

A pale yellow oil stable at or below room temperature for about 12 months in sealed original containers without exposure to direct sunlight. The oil is processed from fish species containing high amounts of omega-3 fatty acids. It is neutralised, bleached, winterised and deodorised. The oil may be purified with shortpath distillation. FFA from fish oil, lemon flavor and mixed tocopherols are added to the oil. An exemplary formulation is shown in Table 13.

TABLE 13

An exemplary formulation of a FFA extract in fish oil.

| Analytical parameters: | Specification |
|---|---|
| Free fatty acids(%) | 1.8-2.5 |
| Acid value (mg KOH/g) | 3.6-5.0 |
| Unsaponifiable matter (in pure oil) (%) | max. 1.5 |
| Eicosapentaenoic acid (EPA) (area %) | min. 18.0 |
| Eicosapentaenoic acid (EPA) (mg/g as FFA) | 150-180 |
| Docosahexaenoic acid (DHA) (area %) | min. 12.0 |
| Docosahexaenoic acid (DHA) (mg/g as FFA) | 100-135 |
| Total omega-3 fatty acids (mg/g as FFA) | 320-360 |
| Cold test; remains clear at 0° C. (hours) | min. 3 |
| Peroxide value (meq. $O_2$/kg) | max. 5.0 |
| Anisidine value | max. 20.0 |
| Lemon flavor (I303) (w/w %) | min. 1 |
| Mixed tocopherols (mg/kg) | min. 1000 |

REFERENCES

The following publications, references, patents and patent applications are hereby incorporated by reference in their entireties.

D. M. Pereira, J. Vinholes, G. Correia-da-Silva, P. Valentao, N. Teixeira, P. B. Andrade, Fatty acids in marine organisms: In the pursuit of bioactive agents, Current Pharmaceutical Analysis, 7 (2011) 108-119.

B. Ilievska, T. Loftsson, M. A. Hjalmarsdottir, G. M. Asgrimsdottir, Topical formulation comprising fatty acid extract from cod liver oil: development, evaluation and stability studies, Marine Drugs, 14(6) (2016).

T. Loftsson, B. Ilievska, G. M. Asgrimsdottir, O. T. Ormarsson, E. Stefansson, Fatty acids from marine lipids: biological activity, formulation and stability of fatty acids from cod-liver oil, J. Drug Deliv. Sci. Technol., 34, 71-75 (2016).

T. Kristmundsdóttir, S. Skúlason, Lipids as active ingredients in pharmaceuticals, cosmetics and health foods, in: H. Thormar (Ed.) Lipids and essential oils as antimicrobial agents, Wiley, Chichester, 2011, pp. 151-177.

A. P. Desbois, K. C. Lawlor, Antibacterial activity of long-chain polyunsaturated fatty acids against *Propionibacterium acnes* and *Staphylococcus aureus*, Mar Drugs, 11 (2013) 4544-4557.

GULL HAFSINS. HG Johnson and S Jonsdottir, Reykjavik 2008.

T. Loftsson, B. Ilievska, G. M. Asgrimsdottir, O. T. Ormarsson, E. Stefansson, Fatty acids from marine lipids: biological activity, formulation and stability of fatty acids from cod-liver oil, J. Drug Deliv. Sci. Technol., 34, 71-75 (2016).

T. Loftsson, E. Stefansson: Fatty acids for use as a medicament. U.S. Pat. No. 9,072,714B2, 7 Jul. 2015.

J. J. Kabara, R. Vrable, M. S. F. Lie Ken Jie, Antimicrobial lipids: natural and synthetic fatty acids and monoglycerides, Lipids, 12 (1977) 753-759.

H. Thormar, Lipids and essential oils as antimicrobial agents, Wiley, Chichester, 2011.

T. Loftsson, H. Thormar, J. H. Ólafsson, T. M. Gunnarsdóttir, B. Hjaltason, G. Gudmundsson, Fatty acid extract from cod-liver oil: activity against herpes simplex virus and enhancement of transdermal delivery of acyclovir in-vitro, Pharm Pharmacol. Commun., 4 (1998) 287-291.

C E Isaacs, H Thormar, T Pessolano, Membrane-disruptive effect of human milk: inactivation of enveloped viruses, J Infect Dis, 154 (6), 966-71, 1986.

H. Thormar, C. E. Isaacs, K. S. Kim, H. R. Brown, Inactivation of visna virus and other enveloped virus is by free fatty acids and monoglycerides, Ann. N.Y. Acad. Sci. 724, 465-471, 1994.

H. Thormar, H. Hilmarsson, The role of microbicidal lipids in host defense against pathogens and their potential as therapeutic agents, Review Chem Phys Lipids, 150 (1), 1-11, 2007.

U. N. Das, Arachidonic acid and other unsaturated fatty acids and some of their metabolites function as endogenous antimicrobial molecules: a review, Review J Adv Res, 11, 57-66, 2018.

E. Revici, B, E. Sherwood; H. P. Benecke, J. M. Rice, R. W. Geisler, Virucidal compositions and therapy, U.S. Pat. No. 4,513,008, 23 Apr. 1985.

H. Hilmarsson, T. Kristmundsdóttir, E. Gunnarsson, H. Thormar; J., Intranasal delivery of formulations containing virucidal lipid for treatment of respiratory syncytial virus, DRUG DEL. SCI. TECH., 23 (5) 455-457 2013.

Hilmarsson H, Traustason B S, Kristmundsdóttir T, Thormar H. Virucidal activities of medium- and long-chain fatty alcohols, fatty acids and monoglycerides against respiratory syncytial virus and parainfluenza virus type 2: Comparison at different pH levels. Arch. Virol. 152, 2225-2236, 2007.

H Thormar, C E. Isaacs, K. S. Kim, H. R. Brown, Inactivation of visna virus and other enveloped viruses by free fatty acids and monoglycerides, Ann N Y Acad Sci, 724, 465-71, 1994.

Y. Yang, F. Peng, R. Wang, K. Guan, T. Jiang, G. Xu, J. Sun, J. Chang, The deadly coronaviruses: The 2003 SARS pandemic and the 2020 novel coronavirus epidemic in China, Autoimmun. 2020 Mar. 3:102434.

U.S. Pat. No. 4,002,775 A.

Remington's Pharmaceutical Sciences, Mack Publishing Company, Philadelphia, Pa., 17th ed. (1985).

A. Joshua A. B. Jackman, Y. Kyeong, L. Danlin, and C. Nam-Joon, Nanotechnology Formulations for Antibacterial Free Fatty Acids and Monoglycerides, Molecules 2016, 21(3), 305.

Reed L, Muench H (1938) A simple method of estimating fifty percent endpoints. American Journal of Hygiene 27: 493-497.

Qing H, Yang Z, Shi M, and Zhang Z, New evidence of SARS-COV-2
transmission through the ocular surface, Graefes Arch Clin Exp Ophthalmol. 2020 May 4: 1-2.

Kristinsson, Kristinsdottir, Blondal, Thormar, Kristjansson, Karason, Sigvaldason, Sigurdsson, Nationwide Incidence and Outcomes of Patients With Coronavirus Disease 2019 Requiring Intensive Care in Iceland, Crit Care Med. 2020 Aug. 18: 10.1097.

What is claimed is:

1. A method of substantially minimizing a respiratory illness in an individual subject in need thereof, the method comprising intra-orally administering to the subject an antiviral formulation comprising an effective amount of a free fatty acid (FFA) mixture,
    wherein the FFA mixture comprises at least two fatty acids selected from the group consisting of myristic acid, palmitic acid, stearic acid, palmitoleic acid, cis-vaccenic acid, oleic acid, gadoleic acid, gondoic acid, erucic acid, cetoleic acid, linoleic acid, α-linolenic acid, moroctic acid, eicosapentaenoic acid (EPA) and docosahexaenoic acid (DHA),
    wherein the amount of the FFA mixture is from about 0.1 to about 20% (v/v),
    wherein the respiratory illness is caused by a coronavirus selected from the group consisting of human coronavirus 229E (hCoV-229E) and the SARS-COV-2.

2. The method of claim 1, wherein the coronavirus is SARS-COV-2.

3. The method of claim 1, wherein the coronavirus when contacted by the antiviral formulation has a log reduction value (LRV) that is comparable to an LRV observed when the same coronavirus is contacted by a solution of 35% (v/v) ethanol.

4. The method of claim 1, wherein the LRV for the coronavirus when contacted by the antiviral formulation is from about 1 to about 4.

5. The method of claim 4, wherein the LRV is from about 1.5 to about 4.0.

6. The method of claim 4, wherein the LRV is from about 2.0 to about 4.0.

7. The method of claim 4, wherein the LRV is from about 2.5 to about 4.0.

8. The method of claim 4, wherein the LRV is from about 3.0 to about 4.0.

9. The method of claim 4, wherein the LRV is from about 3.5 to about 4.0.

10. The method of claim 1, wherein the antiviral formulation inactivates and/or inhibits replication of the coronavirus by at least about 90% of the viral replication.

11. The method of claim 10, wherein the antiviral formulation inactivates and/or inhibits replication of the coronavirus by from about 90.00% to about 99.99%.

12. The method of claim 10, wherein the antiviral formulation inactivates and/or inhibits replication of the coronavirus by from about 96.84% to about 99.99%.

13. The method of claim 10, wherein the antiviral formulation inactivates and/or inhibits replication of the coronavirus by from about 99.00% to about 99.99%.

14. The method of claim 10, wherein the antiviral formulation inactivates and/or inhibits replication of the coronavirus by from about 99.68% to about 99.99%.

15. The method of claim 10, wherein the antiviral formulation inactivates and/or inhibits replication of the coronavirus by from about 99.90% to about 99.99%.

16. The method of claim 10, wherein the antiviral formulation inactivates and/or inhibits replication of the coronavirus by from about 99.97% to about 99.99%.

17. The method of claim 1, wherein the amount of the FFA mixture in the antiviral formulation is selected from the group consisting of from about 0.5% to about 20% (v/v), from about 1% to about 20% (v/v), from about 2% to about 20% (v/v), from about 1% to about 10%, from about 2% to about 10%, from about 1% to about 5% (v/v), and from about 2% to about 5% (v/v), about 1% (v/v), about 1.5% (v/v), about 2% (v/v), and about 2.5% (v/v).

18. The method of claim 1, wherein the FFA mixture when administered at a site of administration has a local concentration selected from the group consisting of from about 0.5% to about 20% (v/v), from about 1% to about 20% (v/v), from about 2% to about 20% (v/v), from about 1% to about 10%, from about 2% to about 10%, from about 1% to about 5% (v/v), from about 2% to about 5% (v/v), about 1% (v/v), about 1.5% (v/v), about 2% (v/v), and about 2.5% (v/v).

19. The method of claim 18, wherein the local concentration remains substantially constant for a minimal period of time at the site of administration and a maximum period of time at the site of administration;
    wherein the minimum period of time is a time period from about 1 second to 10 minutes; and/or
    wherein the maximum period of time is a time period before a significant side effect is observed; and
    wherein optionally the maximum period of time is a time period from about 10 minutes to about 120 minutes; and
    wherein optionally the significant side effect is an irritation observed following administration of the antiviral formulation.

20. The method of claim 19, wherein the minimum period of time is about 5 minutes.

21. The method of claim 19, wherein the minimum period of time is about 10 minutes.

22. The method of claim 1, wherein the antiviral formulation further comprises an additional active ingredient selected from the group consisting of an antiviral, an antibiotic, an antifungal, and combinations thereof.

23. The method of claim 1, wherein the FFA mixture comprises at least two fatty acids selected from the group consisting of palmitoleic acid, cis-vaccenic acid, oleic acid, gadoleic acid, gondoic acid, erucic acid, cetoleic acid, linoleic acid, α-linolenic acid, moroctic acid, eicosapentaenoic acid (EPA), docosahexaenoic acid (DHA) and combinations thereof.

24. The method of claim 1, wherein the FFA mixture comprises one or more saturated or unsaturated fatty acids with a carbon chain length in the range from C14 to C22.

25. The method of claim 1, wherein the FFA mixture is derived from a marine organism.

26. The method of claim 25, wherein the FFA mixture is derived from a fish.

27. The method of claim 25, wherein the FFA mixture is combined with a lipophilic solution.

28. The method of claim 27, wherein the lipophilic solution is an oil derived from the group consisting of a marine organism, a fish, a fish-liver, and/or combinations thereof.

29. The method of claim 1, wherein the antiviral formulation is administered in a mouthwash solution, a throat wash solution, a gargle solution, a liquid-filled lozenge, a liquid-filled tablet, a liquid-filled capsule, a beverage, a syrup, a mouth spray, a throat spray, or combinations thereof.

30. The method of claim 1,
wherein the antiviral formulation is a mouth wash,
wherein the amount of the FFA mixture in the antiviral formulation is from 2% to about 2.5% (v/v),
wherein the FFA mixture is combined with a fish oil, and
wherein the antiviral formulation is administered to the subject at a volume of 5 mL from about 2 to about 4 times a day and for about 1 week.

* * * * *